United States Patent
Maini

(10) Patent No.: US 11,707,321 B2
(45) Date of Patent: Jul. 25, 2023

(54) DIRECTIONAL BALLOON TRANSSEPTAL INSERTION DEVICE FOR MEDICAL PROCEDURES WITH IMPROVED TRANSSEPTAL PUNCTURE SYSTEM WITH PUNCTURE MEMBER BALLOON SEAL

(71) Applicant: EAST END MEDICAL LLC, Lewes, DE (US)

(72) Inventor: Brijeshwar S. Maini, West Palm Beach, FL (US)

(73) Assignee: East End Medical, LLC, Lewes, DE (US)

( * ) Notice: Subject to any disclaimer, the term of this patent is extended or adjusted under 35 U.S.C. 154(b) by 593 days.

(21) Appl. No.: 16/897,472

(22) Filed: Jun. 10, 2020

(65) Prior Publication Data

US 2020/0390495 A1 Dec. 17, 2020

Related U.S. Application Data

(60) Provisional application No. 62/859,943, filed on Jun. 11, 2019.

(51) Int. Cl.
*A61B 18/14* (2006.01)
*A61B 17/34* (2006.01)
(Continued)

(52) U.S. Cl.
CPC ...... *A61B 18/1492* (2013.01); *A61B 17/3496* (2013.01); *A61B 2017/00247* (2013.01);
(Continued)

(58) Field of Classification Search
CPC ............ A61B 18/1492; A61B 17/3496; A61B 2017/00247; A61B 2017/3413; A61B 2018/0022; A61B 2018/0038
See application file for complete search history.

(56) References Cited

U.S. PATENT DOCUMENTS 4,696,304 A 9/1987 Chin
4,813,934 A 3/1989 Engelson et al.
(Continued)

FOREIGN PATENT DOCUMENTS

AU 2017346559 A1 5/2019
AU 2018307956 A1 2/2020
(Continued)

OTHER PUBLICATIONS

First Office Action dated May 7, 2021, from Chinese Application No. 201780074077.5, 15 sheets.
(Continued)

*Primary Examiner* — Michael F Peffley
*Assistant Examiner* — Bo Ouyang
(74) *Attorney, Agent, or Firm* — FisherBroyles, LLP; Rachel H. Huffstetler

(57) ABSTRACT

The disclosed invention provides a transseptal insertion device which is suitable for facilitating precise and safe transseptal puncture of a cardiac interatrial septum. The transseptal insertion device includes a sheath that defines at least one lumen therein, one or more positioning balloons that are connected to a distal end of the sheath, a puncture member movably positioned within the at least one lumen, and a puncture member balloon located on the puncture member. The sheath has one or more deflation ports to deflate the one or more positioning balloons. The puncture member balloon, when inflated, is capable of sealing the one or more deflation ports in the sheath, permitting the inflation of the one or more positioning balloons. When the puncture member moves toward fossa ovalis, the inflated puncture member balloon moves away from the deflation ports, allowing the positioning balloons to be deflated.

15 Claims, 24 Drawing Sheets

(51) Int. Cl.
 *A61B 17/00* (2006.01)
 *A61B 18/00* (2006.01)
(52) U.S. Cl.
 CPC .............. *A61B 2017/3413* (2013.01); *A61B 2018/0022* (2013.01); *A61B 2018/0038* (2013.01)

(56) References Cited

U.S. PATENT DOCUMENTS

| | | |
|---|---|---|
| 5,135,001 A | 8/1992 | Sinofsky et al. |
| 5,295,958 A | 3/1994 | Shturman |
| 5,699,805 A | 12/1997 | Seward et al. |
| 5,792,118 A | 8/1998 | Kurth et al. |
| 5,865,801 A | 2/1999 | Houser |
| 6,017,323 A | 1/2000 | Chee |
| 6,102,907 A | 8/2000 | Smethers |
| 6,102,926 A | 8/2000 | Targalia et al. |
| 6,129,672 A | 10/2000 | Seward et al. |
| 6,231,588 B1 | 5/2001 | Zadno-Azizi |
| 6,440,097 B1 | 8/2002 | Kupiecki |
| 6,540,712 B1 | 4/2003 | Parodi et al. |
| 7,666,203 B2 | 2/2010 | Chanduszko et al. |
| 7,678,081 B2 | 3/2010 | Whiting et al. |
| 8,096,959 B2 | 1/2012 | Stewart et al. |
| 8,900,214 B2 | 12/2014 | Nance et al. |
| 9,072,872 B2 | 7/2015 | Asleson et al. |
| 9,510,904 B2 | 12/2016 | Krishnan |
| 9,545,265 B2 | 1/2017 | Maisano et al. |
| 9,700,351 B2 | 7/2017 | Maisano et al. |
| 9,757,137 B2 | 9/2017 | Krolik et al. |
| 2003/0019546 A1 | 1/2003 | Kanekiyo et al. |
| 2003/0023204 A1 | 1/2003 | Vo et al. |
| 2003/0229386 A1 | 12/2003 | Rosenman et al. |
| 2004/0215233 A1 | 10/2004 | Kaplan |
| 2005/0065419 A1 | 3/2005 | Partridge et al. |
| 2005/0159738 A1 | 7/2005 | Visram et al. |
| 2005/0197530 A1 | 9/2005 | Wallace |
| 2005/0245822 A1 | 11/2005 | Dala-Krishna et al. |
| 2006/0009715 A1 | 1/2006 | Khairkhahan |
| 2007/0149995 A1 | 6/2007 | Quinn et al. |
| 2007/0270751 A1 | 11/2007 | Stangenes et al. |
| 2007/0293724 A1 | 12/2007 | Saadat et al. |
| 2008/0132937 A1 | 6/2008 | Hartley |
| 2008/0171989 A1 | 7/2008 | Bell |
| 2008/0243081 A1 | 10/2008 | Nance |
| 2008/0262596 A1 | 10/2008 | Xiao |
| 2009/0076498 A1 | 3/2009 | Saadat et al. |
| 2009/0259272 A1 | 10/2009 | Reddy et al. |
| 2010/0010488 A1 | 1/2010 | Kassab |
| 2010/0168777 A1 | 7/2010 | Stangenes et al. |
| 2010/0174189 A1 | 7/2010 | Abraham |
| 2010/0286718 A1 | 11/2010 | Kassab |
| 2011/0270239 A1 | 11/2011 | Werneth |
| 2011/0295268 A1 | 12/2011 | Roelle |
| 2012/0203169 A1 | 8/2012 | Tegg |
| 2012/0259263 A1 | 10/2012 | Celermajer |
| 2013/0090649 A1 | 4/2013 | Smith |
| 2013/0102862 A1* | 4/2013 | Mercader ........... A61B 5/14546 600/317 |
| 2014/0039494 A1 | 2/2014 | Kick et al. |
| 2014/0081301 A1 | 3/2014 | Tran |
| 2014/0171903 A1 | 6/2014 | Roman et al. |
| 2014/0276027 A1 | 9/2014 | Gaddis |
| 2014/0309675 A1* | 10/2014 | Maisano ........... A61B 17/3478 606/170 |
| 2015/0165170 A1 | 6/2015 | Beasley |
| 2015/0173794 A1 | 6/2015 | Kurth et al. |
| 2015/0216620 A1 | 8/2015 | Davies et al. |
| 2015/0217093 A1 | 8/2015 | Tsutsui |
| 2015/0224240 A1 | 8/2015 | Farnan et al. |
| 2015/0258270 A1 | 9/2015 | Kunis |
| 2015/0306359 A1 | 10/2015 | Drasler |
| 2016/0008636 A1 | 1/2016 | Warnking |
| 2016/0051321 A1 | 2/2016 | Salahieh et al. |
| 2016/0081704 A1 | 3/2016 | Jeon et al. |
| 2016/0100860 A1 | 4/2016 | Lenker et al. |
| 2016/0143522 A1 | 5/2016 | Ransbury et al. |
| 2016/0193449 A1 | 7/2016 | Sarabia et al. |
| 2016/0279393 A1 | 9/2016 | Anderson et al. |
| 2017/0105761 A1 | 4/2017 | Sapir |
| 2017/0135559 A1 | 5/2017 | Horrisberger et al. |
| 2017/0143940 A1 | 5/2017 | Flygare |
| 2018/0103985 A1 | 4/2018 | Maini |
| 2018/0177516 A1 | 6/2018 | Vardi |
| 2018/0264231 A1 | 9/2018 | Scheibe et al. |
| 2019/0000544 A1 | 1/2019 | Govari et al. |
| 2019/0029722 A1 | 1/2019 | Maini |
| 2019/0029750 A1 | 1/2019 | Maini |
| 2019/0134412 A1 | 5/2019 | Shuros et al. |
| 2019/0209177 A1 | 7/2019 | Whitfield et al. |
| 2020/0297412 A1 | 9/2020 | Maini |
| 2020/0390495 A1 | 12/2020 | Maini |
| 2021/0085384 A1 | 3/2021 | Maini |
| 2021/0100981 A1 | 4/2021 | Maini |
| 2021/0251553 A1 | 8/2021 | Maini |

FOREIGN PATENT DOCUMENTS

| | | |
|---|---|---|
| AU | 2018307969 A1 | 2/2020 |
| AU | 2020241992 A1 | 10/2021 |
| AU | 2020292273 A1 | 1/2022 |
| AU | 2020349508 A1 | 4/2022 |
| AU | 2020357991 A1 | 4/2022 |
| CA | 3041032 A1 | 4/2018 |
| CA | 3071391 A1 | 1/2019 |
| CA | 3071432 A1 | 1/2019 |
| CA | 3138742 A1 | 9/2020 |
| CA | 3141251 A1 | 12/2020 |
| CA | 3151548 A1 | 3/2021 |
| CA | 3153126 A1 | 4/2021 |
| CL | 2019001078 A1 | 11/2019 |
| CL | 2020000232 A1 | 2/2021 |
| CN | 1599579 A | 3/2005 |
| CN | 101442946 A | 5/2009 |
| CN | 103429179 A | 12/2013 |
| CN | 107530532 A | 1/2018 |
| CN | 110022779 A | 7/2019 |
| CN | 111093539 A | 5/2020 |
| CN | 111148474 A | 5/2020 |
| CN | 113692257 A | 11/2021 |
| CN | 114269270 A | 4/2022 |
| CN | 114727804 A | 7/2022 |
| CN | 114980824 A | 8/2022 |
| CN | 1100227796 | 8/2022 |
| EP | 2233169 A1 | 9/2010 |
| EP | 2459266 A1 | 6/2012 |
| EP | 3528711 A1 | 8/2019 |
| EP | 3528711 A4 | 6/2020 |
| EP | 3658036 A1 | 6/2020 |
| EP | 3658045 A1 | 6/2020 |
| EP | 3941371 A1 | 1/2022 |
| EP | 3982849 A1 | 4/2022 |
| EP | 4037585 A1 | 8/2022 |
| EP | 3253438 B1 | 9/2022 |
| IN | 201917018712 A | 8/2019 |
| IN | 202017008571 A | 8/2020 |
| IN | 202017008345 A | 10/2020 |
| IN | 202217000583 A | 3/2022 |
| IN | 202217016718 A | 7/2022 |
| IN | 202117041934 A | 9/2022 |
| IN | 202217020063 A | 9/2022 |
| JP | H06506853 | 8/1994 |
| JP | H08117232 A | 5/1996 |
| JP | 2009539575 | 11/2009 |
| JP | 2013226429 A | 11/2013 |
| JP | 2019531829 A | 11/2019 |
| JP | 2020530372 A | 10/2020 |
| JP | 2020530373 A | 10/2020 |
| JP | 2022527456 A | 6/2022 |
| JP | 711382062 | 8/2022 |
| JP | 2022536719 A | 8/2022 |
| WO | 02/096264 A2 | 12/2002 |
| WO | 2007147060 A2 | 12/2007 |

(56) References Cited

FOREIGN PATENT DOCUMENTS

| WO | 2014036317 A2 | 3/2014 |
|---|---|---|
| WO | 2015058007 A1 | 4/2015 |
| WO | 2017083785 | 5/2017 |
| WO | 2018033401 A1 | 2/2018 |
| WO | 2018075426 A1 | 4/2018 |
| WO | 2019023609 A1 | 1/2019 |
| WO | 2019023653 A1 | 1/2019 |
| WO | 2019113043 A1 | 6/2019 |
| WO | 2019023653 A8 | 8/2019 |
| WO | 2020191133 A1 | 9/2020 |
| WO | 2020251999 A1 | 12/2020 |
| WO | 2021055572 A1 | 3/2021 |
| WO | 2021067669 A1 | 4/2021 |

OTHER PUBLICATIONS

Written Opinion dated Jun. 16, 2021, from Chilean Patent Application No. 202000403, 16 sheets.
International Search Report and Written Opinion dated May 25, 2021, from International Patent Application No. PCT/US2021/017528, 15 sheets.
International Search Report and Written Opinion for International Application No. PCT/US2020/051228 dated Dec. 1, 2020, 14 sheets.
Final Office Action dated Aug. 18, 2021, from U.S. Appl. No. 15/784,792, 55 sheets.
Communication Pursuant to Article 94(3) EPC dated Aug. 25, 2021, from EP Application No. 18755361.5, 4 sheets.
Office Action dated Sep. 3, 2021, from Chile Application No. 202000232, 20 sheets.
Notice of Reasons for Rejection dated Sep. 28, 2021, from Japanese Application No. 2019-521811, 4 sheets.
International Search Report and Written Opinion dated Oct. 1, 2021, from PCT Application No. PCT/US2021/018409, 17 sheets.
Final Office Action dated Oct. 7, 2021, from U.S. Appl. No. 16/047,910, 29 sheets.
Office Action dated Oct. 6, 2021, U.S. Appl. No. 16/048,005, 81 sheets.
International Search Report and Written Opinion for International Application No. PCT/US2020/036965 dated Sep. 16, 2020, 16 sheets.
Invitation to Respond to Written Opinion from Singapore Patent Application No. 11202000666S, dated Mar. 2, 2021, 11 sheets.
Invitation to Respond to Written Opinion from Singapore Patent Application No. 11202000667S, dated Mar. 2, 2021, 11 sheets.
International Search Report and Written Opinion dated Jan. 13, 2021, from PCT/US2020/53902, 12 sheets.
Non-Final Office Action dated Jan. 26, 2021, from U.S. Appl. No. 15/784,792, 41 sheets.
Final Office Action dated Aug. 4, 2020, from U.S. Appl. No. 15/784,792, 38 sheets.
Non-Final Office Action dated Apr. 30, 2021, from U.S. Appl. No. 16/047,910, 46 sheets.
International Search Report and Written Opinion for International Application No. PCT/US2018/044143 dated Dec. 5, 2018, 16 sheets.
International Search Report and Written Opinion for International Application No. PCT/US2018/044207 dated Oct. 31, 2018, 17 sheets.
International Search Report and Written Opinion for International Application No. PCT/US2020/023518 dated Jun. 23, 2020, 15 sheets.
The extended European search report dated May 12, 2020, from EP Application No. 17862286.6, 8 sheets.
International Search Report and Written Opinion dated Dec. 14, 2017, from PCT/US2017/056843.
Non-Final Office Action dated Feb. 6, 2020, from U.S. Appl. No. 15/784,792, 29 sheets.
EP Application No. 18756031.3, EP Communication dated Oct. 4, 2021, 11 pages.
International Preliminary Report on Patentability PCT/US2017/056843; dated May 2, 2019, 5 pages.
International Preliminary Report on Patentability PCT/US2018/044143; dated Feb. 28, 2020, 9 pages.
International Preliminary Report on Patentability PCT/US2018/044207; dated Feb. 6, 2020, 8 pages.
International Preliminary Report on Patentability PCT/US2020/023518; dated Sep. 30, 2021, 10 pages.
International Preliminary Report on Patentability PCT/US2020/036965; dated Dec. 23, 2021, 8 pages.
International Preliminary Report on Patentability PCT/US2020/051228; dated Mar. 31, 2022, 9 pages.
International Preliminary Report on Patentability PCT/US2020/053902; dated Apr. 14, 2022, 5 pages.

\* cited by examiner

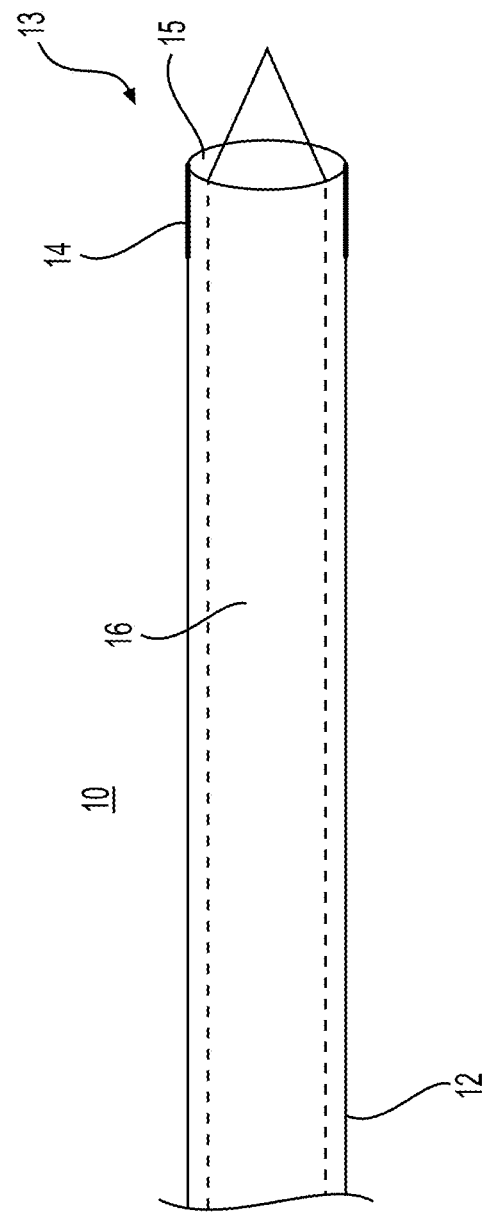

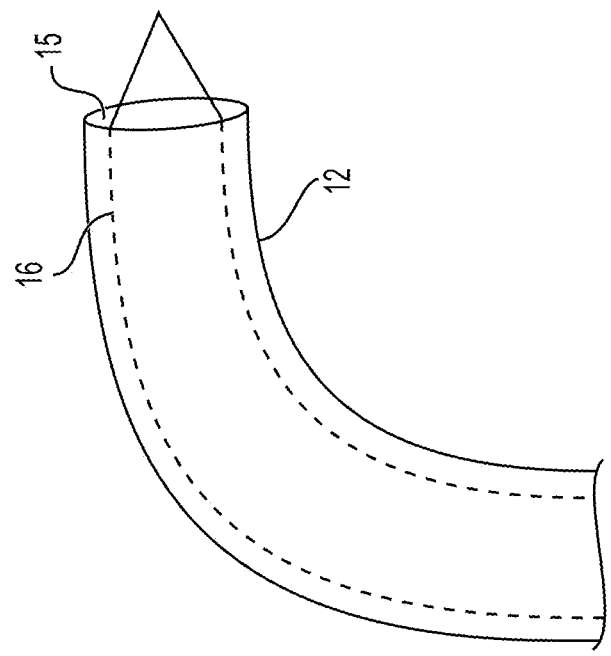
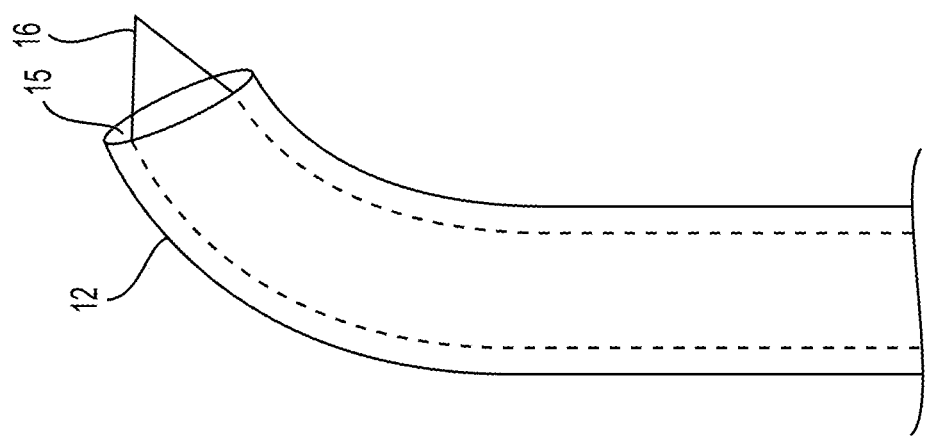
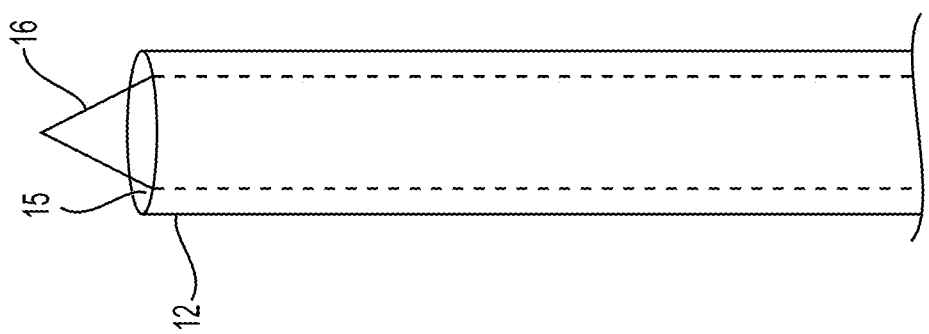
*FIG. 10A*  *FIG. 10B*  *FIG. 10C*

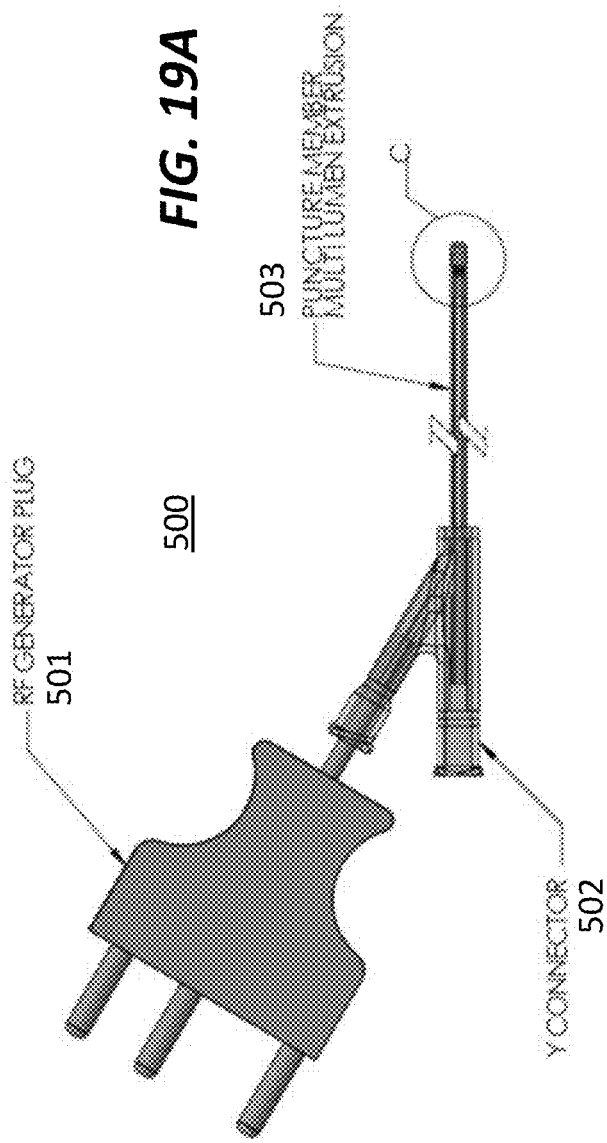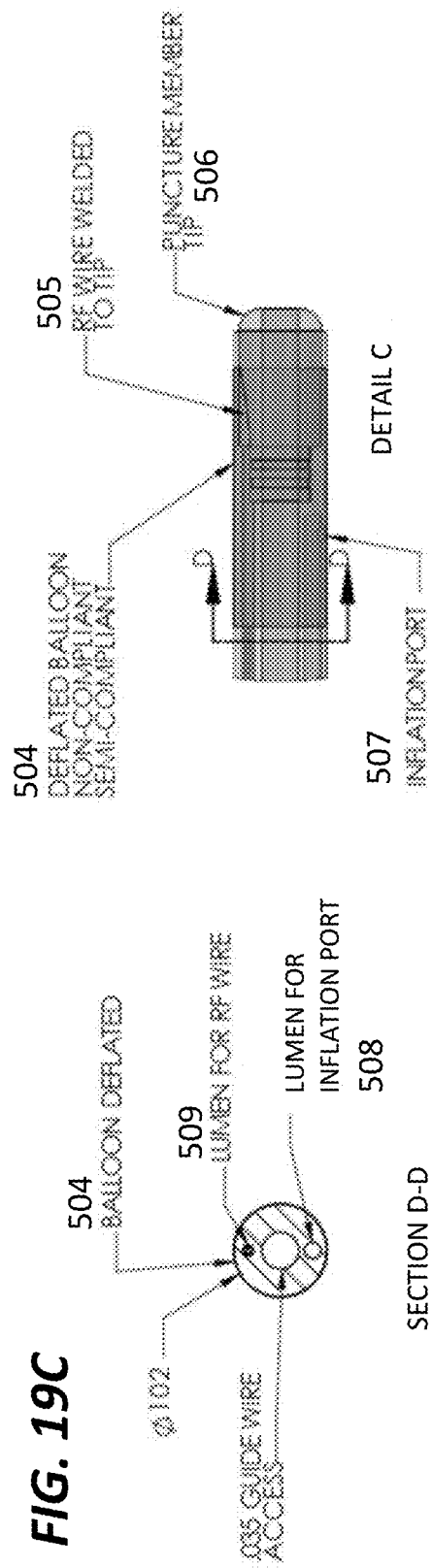

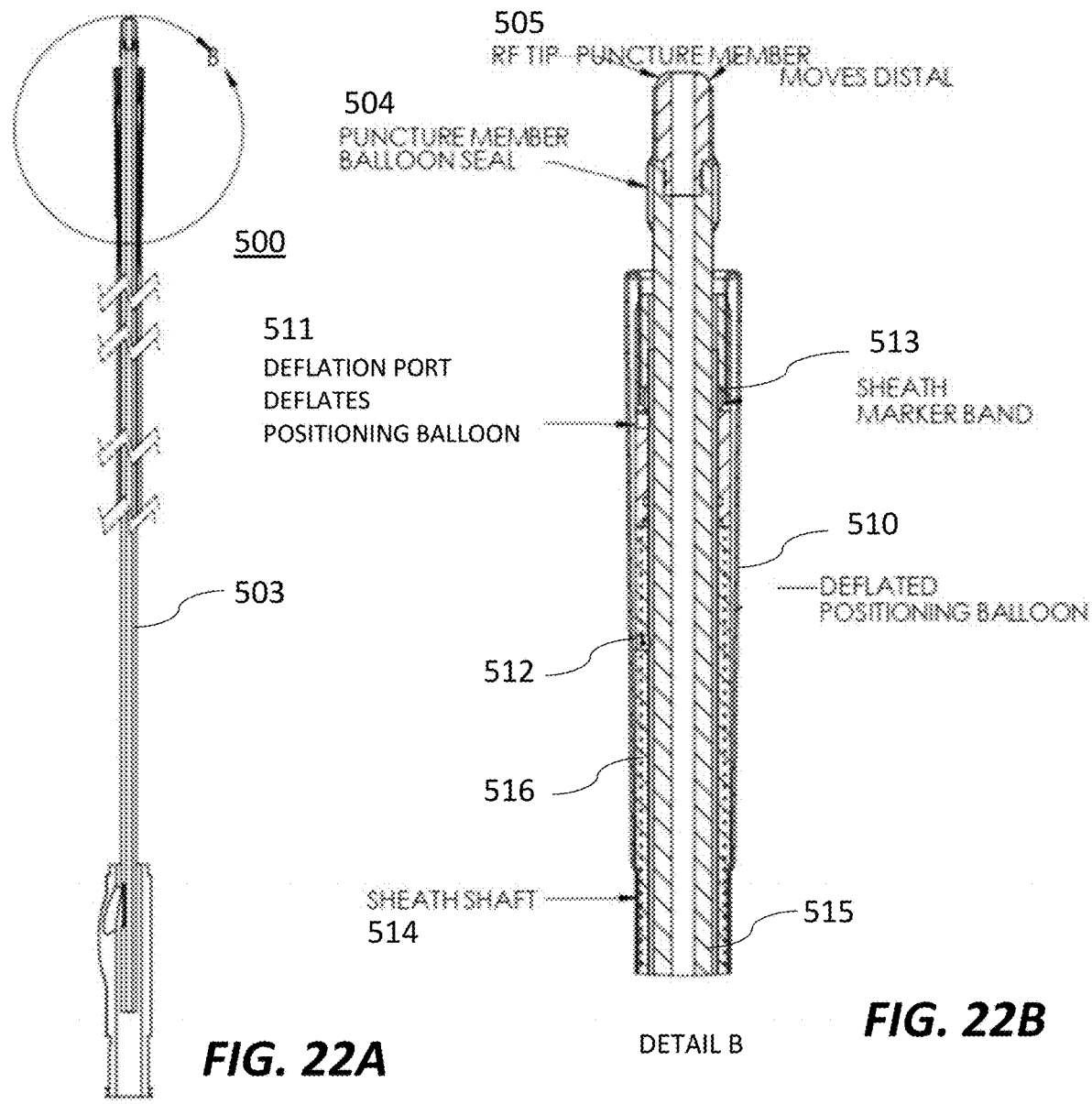

DIRECTIONAL BALLOON TRANSSEPTAL INSERTION DEVICE FOR MEDICAL PROCEDURES WITH IMPROVED TRANSSEPTAL PUNCTURE SYSTEM WITH PUNCTURE MEMBER BALLOON SEAL

CROSS REFERENCE TO RELATED APPLICATIONS

This application claims the priority of U.S. Provisional Application Ser. No. 62/859,943, filed on Jun. 11, 2019, which is hereby incorporated herein by reference in its entirety.

FIELD

The present invention relates generally to cardiac catheters, and more particularly, to a transseptal insertion device which is suitable for facilitating quick and safe transseptal puncture and insertion of a catheter through a cardiac septum to provide access to the left atrium in implementation of a left atrial intervention.

BACKGROUND

Cardiac catheterization is a medical procedure in which a long thin tube or catheter is inserted through an artery or vein into specific areas of the heart for diagnostic or therapeutic purposes. More specifically, cardiac chambers, vessels and valves may be catheterized.

Cardiac catheterization may be used in procedures such as coronary angiography and left ventricular angiography. Coronary angiography facilitates visualization of the coronary vessels and finding of potential blockages by taking X-ray images of a patient who has received a dye (contrast material) injection into a catheter previously injected in an artery. Left ventricular angiography enables examination of the left-sided heart chambers and the function of the left sided valves of the heart, and may be combined with coronary angiography. Cardiac catheterization can also be used to measure pressures throughout the four chambers of the heart and evaluate pressure differences across the major heart valves. In further applications, cardiac catheterization can be used to estimate the cardiac output, or volume of blood pumped by the heart per minute.

Some medical procedures may require catheterization into the left atrium of the heart. For this purpose, to avoid having to place a catheter in the aorta, access to the left atrium is generally achieved by accessing the right atrium, puncturing the interatrial septum between the left and right atria of the heart, and threading the catheter through the septum and into the left atrium. Transseptal puncture must be carried out with extreme precision, as accidental puncturing of surrounding tissue may cause very serious damage to the heart. In addition, transseptal puncture may require complicated instruments which are not helpful in guaranteeing the precision of the puncture.

The use of devices available today present many challenges for doctors attempting to puncture the interatrial septum and perform cardiac catheterization. Locating the interatrial septum, properly placing the distal end of the puncturing device at the desired location of the septum, safely puncturing the interatrial septum, avoiding accidental punctures, and tracking and maneuvering the catheter post-puncture, are among the many challenges facing those performing cardiac catheterization today.

SUMMARY

Accordingly, there is an established need for a device that is suitable for facilitating quick and safe transseptal puncturing to provide access to the left atrium in implementation of a left atrial intervention.

These advantages and others are achieved, for example, by a transseptal insertion device which is suitable for facilitating precise and safe transseptal puncture of a cardiac interatrial septum. The transseptal insertion device includes a sheath that defines at least one lumen therein and has a distal end that is positioned toward the cardiac interatrial septum of a patient when the transseptal insertion device is in use and a proximal end that is external to the patient, one or more positioning balloons that are connected to the distal end of the sheath, in which the one or more positioning balloons, when inflated and the transseptal insertion device is in use, overhang and extend past the distal end of the sheath, preventing accidental puncturing of the cardiac interatrial septum and stabilizing the transseptal insertion device against fossa ovalis of the cardiac interatrial septum, and in which the sheath includes one or more deflation ports to deflate the one or more positioning balloons, a puncture member movably positioned within the at least one lumen, in which the puncture member has a distal end that is positioned toward the cardiac interatrial septum of the patient, and a puncture member balloon located on the puncture member, in which the puncture member balloon, when inflated, is capable of sealing the one or more deflation ports of the sheath, permitting the inflation of the one or more positioning balloons.

These advantages and others are also achieved, for example, by a method for suitably facilitating precise and safe transseptal puncture of a cardiac interatrial septum with a transseptal insertion device. The method includes inflating a puncture member balloon located on a puncture member that has a distal end that is positioned toward the cardiac interatrial septum of the patient, sealing one or more deflation ports located in a sheath with the inflated puncture member balloon, inflating one or more positioning balloons connected to a distal end of the sheath, in which the inflated one or more positioning balloons overhang and extend past the distal end of the sheath, positioning the puncture member against fossa ovalis of the cardiac interatrial septum while the positioning balloons are inflated, advancing the puncture member toward the fossa ovalis, in which the distal end of the puncture member extends past the overhanging one or more positioning balloons, in which the puncture member balloon moves away from the one or more deflation ports while the puncture member advances, and deflating the one or more positioning balloons while the distal end of the puncture member presses the fossa ovalis.

BRIEF DESCRIPTION OF THE DRAWINGS

The preferred embodiments described herein and illustrated by the drawings hereinafter be to illustrate and not to limit the invention, where like designations denote like elements.

FIG. 1A is a side perspective, cross-sectional view of an embodiment of a transseptal insertion device.

FIG. 1B is a side perspective, cross-sectional view of an embodiment of a transseptal insertion device showing a dilator extending partially through and extending out from device.

FIGS. 10A-10C are perspective, cross-sectional views of an embodiment of a flexible transseptal insertion device with different angulations.

FIGS. 19A-19C are a side view, a cross-sectional end view, and a close side view of a puncture tip of an embodiment of an improved transseptal puncture system with puncture member balloon seal with a deflated puncture member balloon.

FIGS. 22A-22B are cross-sectional side view and a close, cross-sectional side view of a puncture tip of an embodiment of an improved transseptal puncture system with puncture member balloon seal with a deflated positioning balloon.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1C:
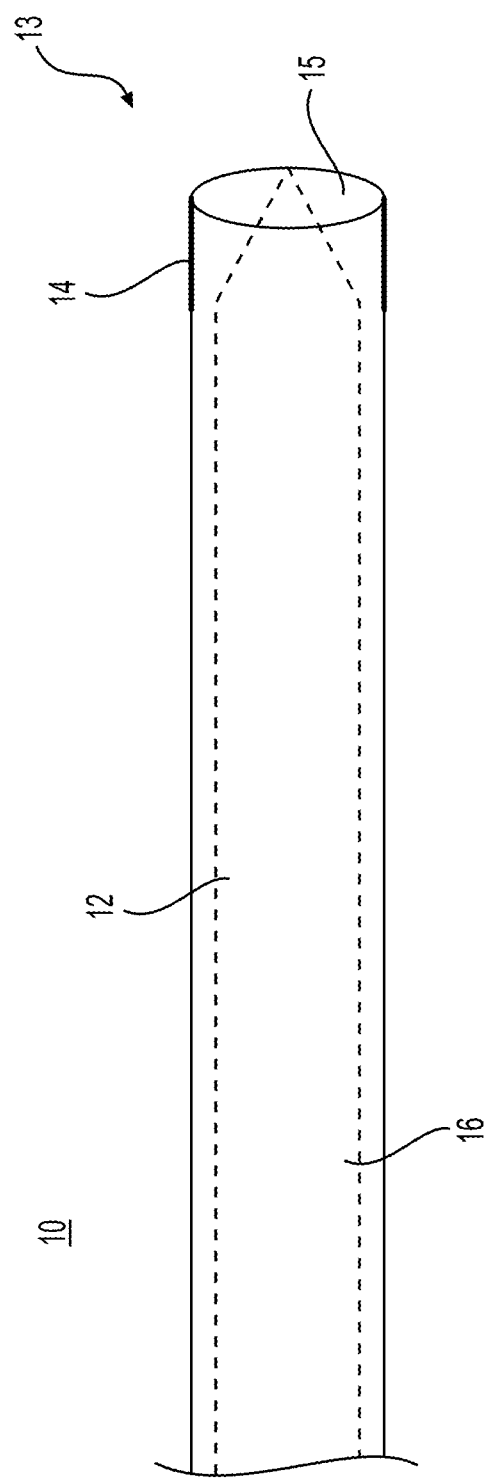
FIG. 1C is a side perspective, cross-sectional view of an embodiment of a transseptal insertion device showing a dilator extending partially through the device.

With reference to FIGS. 1A-1C, shown is an embodiment of transseptal insertion device or catheter 10. Shown is the distal end of transseptal insertion device 10, i.e., the end of transseptal insertion device 10 with opening through which dilator, catheter, and needle may extend, e.g., to puncture interatrial cardiac septum. As shown in FIG. 1A, transseptal insertion device 10 includes outer sheath or balloon shaft 12 and one or more balloons 14 located at distal tip 13 of transseptal insertion device 10. Sheath 12 may contain and define a center lumen 15. Sheath 12 may be fabricated from various materials, including, e.g., polymers, including thermoplastics elastomers (TPEs) such as PEBA (e.g., Pebax®), nylons, thermoplastic polyurethanes (TPUs) such as Pellathane®, similar materials and combinations thereof. Sheath 12 may be referred to as catheter shaft and used in cardiac catheterizations. After puncture, sheath 12 may be inserted through septum into left atrium. Alternatively, sheath 12 may contain a separate catheter that is inserted through septum post puncture. Transseptal insertion device 10 also includes dilator 16, positioned in center lumen 15, as shown in FIG. 1B. The one or more balloons 14 are preferably sealed, air-tight and water-tight, on both its ends to sheath 12.

With continuing reference to FIG. 1A, in view shown, overhanging one or more balloons 14 are uninflated. Although cross-section of balloons 14 shown on top and bottom of distal tip 13, balloons 14 preferably extend around circumference of distal tip or end 13 of transseptal insertion device 10. Overhanging one or more balloons 14 are of form such that balloons 14 overhang or extend from distal tip 13 of sheath 12 when inflated.

In FIG. 1B, dilator 16 is shown positioned within and partially extending out of sheath 12, past distal tip 13 of device 10. Overhanging one or more balloons 14 are uninflated and dilator 16 extends past balloons 14. It is noted that the relative sizes of sheath 12 and dilator 16 shown are for illustrative purposes as the diameter of dilator 16 may be relatively larger or smaller than shown in relation to the diameter of sheath 12, although dilator 16 necessarily has a smaller diameter than sheath 12. Although dilator 16 is shown to have a pointed end, dilator 16 may have a rounded or relatively flat end. Embodiments, as described herein, are designed and intended to puncture septum without use of a needle or other sharp instrument.

With reference now to FIG. 1C, dilator 16 is shown positioned within center lumen 15 of sheath 12. Tip of dilator 16 is positioned within distal tip 13 of transseptal insertion device 10 sub-planar to end of transseptal insertion device 10. The position shown is position dilator 16 may be in immediately prior to inflation of one or more balloons 14. It is noted that the relative sizes of catheter/sheath 12 and dilator 16 shown are for illustrative purposes as the diameter of dilator 16 may be relatively larger or smaller than shown in relation to the diameter of sheath 12. Ordinarily, dilator 16 has smaller diameter or gauge then catheter/sheath 12, although fit of dilator 16 in catheter/sheath 12 is preferably snug enough so that dilator 16 does not move (laterally or axially) relative to position or "wobble" within transseptal insertion device 10. Dilator 16 necessarily has a smaller diameter than sheath 12. In embodiments, sheath 12 material may be sufficiently malleable to enable larger diameter dilators 16, and other larger diameter devices, to be passed through sheath 12. In such embodiments, sheath 12 will stretch to accommodate the larger diameter dilator 16 or other device.

Figure 2A:
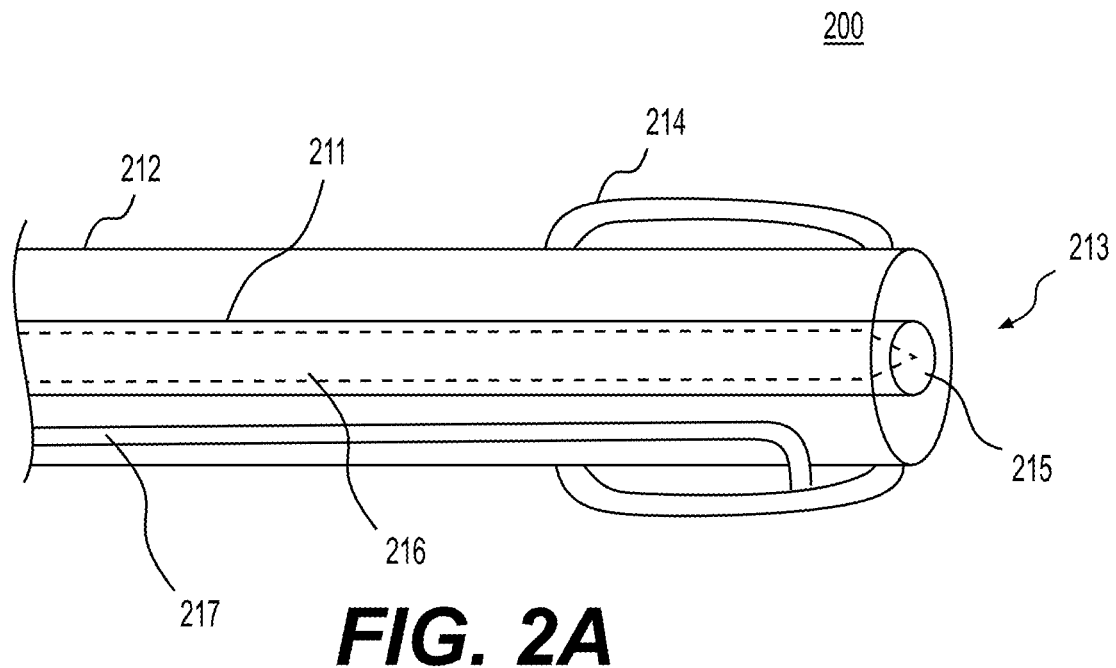
FIG. 2A is a is a perspective view of an embodiment of a transseptal insertion device with hypotube connected to one or more balloons.
Figure 2B:
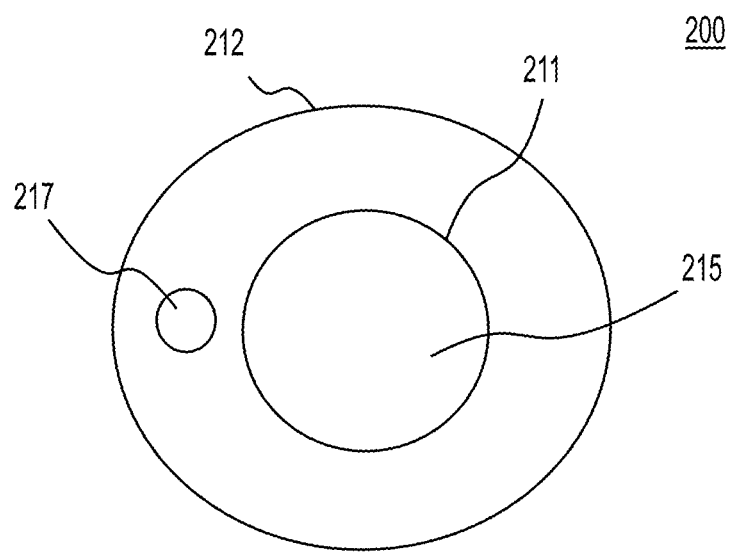
FIG. 2B is a is a front view of an embodiment of a transseptal insertion device with hypotube connected to one or more balloons.

With reference to FIG. 2A, shown is a side perspective view of an embodiment of transseptal insertion device or catheter 200. Shown is the distal end of transseptal insertion device 200, i.e., the end of transseptal insertion device 200 with opening through which dilator, catheter, and needle may extend, e.g., to puncture interatrial cardiac septum. In the embodiments described herein, needle may be a sharpened needle for piercing or puncturing the interatrial cardiac septum or may be equipped to deliver energy to pierce or puncture the interatrial cardiac septum. As shown in FIG. 2A, transseptal insertion device 200 includes outer sheath or catheter shaft 212 and one or more balloons 214 located at distal tip 213 of transseptal insertion device 200. Sheath 212 may contain lumen shaft 211 that defines center lumen 215. Sheath 212 may be fabricated from various materials, including, e.g., polymers, including thermoplastics elastomers (TPEs) such as PEBA (e.g., Pebax®), nylons, thermoplastic polyurethanes (TPUs) such as Pellathane®, similar materials and combinations thereof. Sheath 212 may be referred to as catheter shaft and used in cardiac catheterizations. After puncture, sheath 212 may be inserted through septum into left atrium. Alternatively, sheath 212 may contain multiple lumen shafts that define multiple lumens separately. Transseptal insertion device 200 also includes dilator 216, positioned in center lumen 215. The one or more balloons 214 are preferably sealed, air-tight and water-tight, on both their ends to sheath 212. Transseptal insertion device 200 includes hypotube 217 for inflation or deflation of one or more balloons 214. Hypotube 217 may be contained in sheath or catheter shaft 212. Transseptal insertion device 200 may further include a port (not shown) connected to hypotube 217 to supply gas or fluid to inflate one or more balloons 214, or to remove gas or fluid from one or more balloons 214 to deflate balloons 214. Balloons 214 may be fully inflated or deflated, or may be inflated or deflated as much as desired. With reference to FIG. 2B, shown is a front, cross-sectional view of distal end 213 of the embodiment of transseptal insertion device 200 that shows cross-sectional views of sheath 212, center lumen 215, and hypotube 217.

Figure 2D:
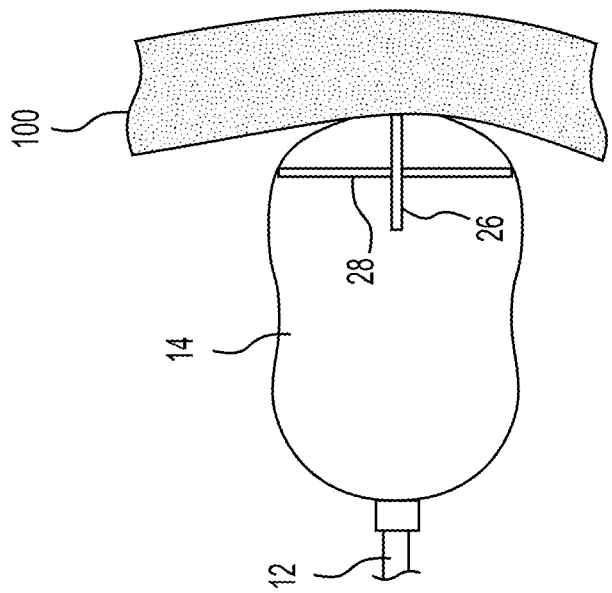
FIGS. 2C-2D are side views of embodiments of transseptal insertion device with ultrasound imaging or visualizing capability.
Figure 2C:
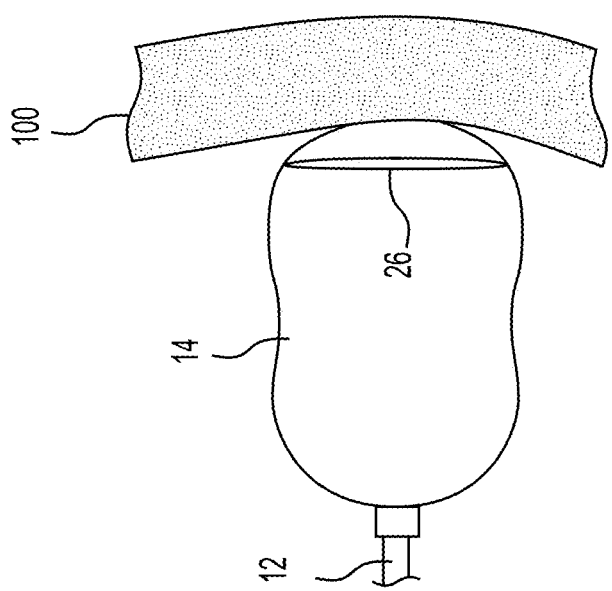

In the embodiment shown in FIGS. 2A and 2B, transseptal insertion device 200 may include ultrasound chips or transducers 26 for ultrasound imaging or visualizing (see FIGS. 2C-2D). The transseptal sheath 212 or balloon 214 may house (inside or on) an ultrasound chip or transducer which may be used to guide the insertion procedure. Ultrasound chip or transducer emits and receives ultrasound energy, that may be detected by known ultrasound visualization devices, to create an image of the cardiac chambers (e.g., the right atrium, fossa, interatrial septum, left atrium, atrial appendage, mitral valve, ventricle, etc.). Ultrasound chips and transducers are transducers that convert ultrasound waves to electrical signals and/or vice versa. Those that both transmit and receive may also be called ultrasound transceivers; many ultrasound sensors besides being sensors are indeed transceivers because they can both sense and transmit. Such imaging will allow the operator(s) of transseptal insertion device 200 to visualize the cardiac chambers and the determine the location of the distal end or tip 213 of transseptal insertion device 200, enabling more precise operation of transseptal insertion device 200. Such a ultrasound chips or transducers used may be similar to ultrasound chip or transducer described in US Pat. App. Pub. 2003/019546, which is herein incorporated by reference, or any other ultrasound transducer known to those of ordinary skill in the art that may be fabricated on scale small enough to be deployed on or in sheath 212 or balloon 214.

With reference to FIGS. 2C-2D, shown are embodiments of transseptal insertion device 200 with ultrasound imaging or visualizing capability. Balloon 14 shown includes one or more ultrasound chips or transducers 26 deployed in or on balloon 14. Ultrasounds chips or transducers 26 may be ultrasound transceivers that both emit and receive waves, convert the ultrasound waves to electrical signals, transmit the electrical signals, e.g., through a wire that runs via sheath 12. Ultrasounds chips or transducers 26 may be connected via WiFi or other wireless connection, to an external imaging device that produces images from the received signals (both still and video images).

Ultrasound chips or transducers 26 may be affixed to interior or exterior surface of balloon 14. Ultrasound chips or transducers 26 may be arranged in a line, disc, or cross-shape. Ultrasound chips or transducers 26 may be arranged to be forward facing (e.g., on distal end of balloon facing towards interatrial septum), as shown in FIG. 2C, or in a different direction/orientation, such as sideways and forward facing (e.g., facing towards interatrial septum and facing perpendicular to the distal or front end), as shown in FIG. 2D. Indeed, orientation of ultrasound chips or transducers 26 may depend on whether balloon 14 is inflated or not. When balloon 14 is fully inflated, as shown in FIG. 2C, ultrasound transducer 26 may be forward facing (or forward and perpendicularly facing as shown in FIG. 2D). However, when balloon 14 is deflated, ultrasound transducer 26 may be folded flat and positioned on side of distal tip 13 of sheath 12. Hence, when balloon 14 is deflated, ultrasound chip or transducer 26 may be side-facing. During inflation ultrasound transducer 26 orientation will change as balloon 14 inflates (moving from side-facing orientation to forward facing orientation with the ultrasound transducer 26 shown in FIG. 2C). Accordingly, operator(s) of transseptal insertion device 200 may vary the inflation of balloon 14 to achieve different orientations of ultrasound transducer 26 for different imaging views.

Ultrasound chip or transducers 26 may emit and/or receive/detect ultrasound waves that may be reflect off of surfaces and structures, e.g., within atrium, and then read by imaging system (not shown), e.g., connected to ultrasound chips or transducers 26 via wire or cable extending through, e.g., lumen 15 in sheath 12. In this manner, ultrasound chips or transducers 26 may enable visualization of the interatrial septum and the left atrial structures.

It is also noted that ultrasound chips or transducers 26 may be deployed on distal tip 13 of sheath 12 (or elsewhere on or in sheath 12). Ultrasound chips or transducers 26 may be installed or configured to be forward facing (facing towards distal end of sheath 12). Alternatively, ultrasound chips or transducers 26 may be flipped to be rear facing (facing towards proximal end of sheath 12). Varying orientations of ultrasound chips or transducers 26 may be implemented.

Figure 3A:
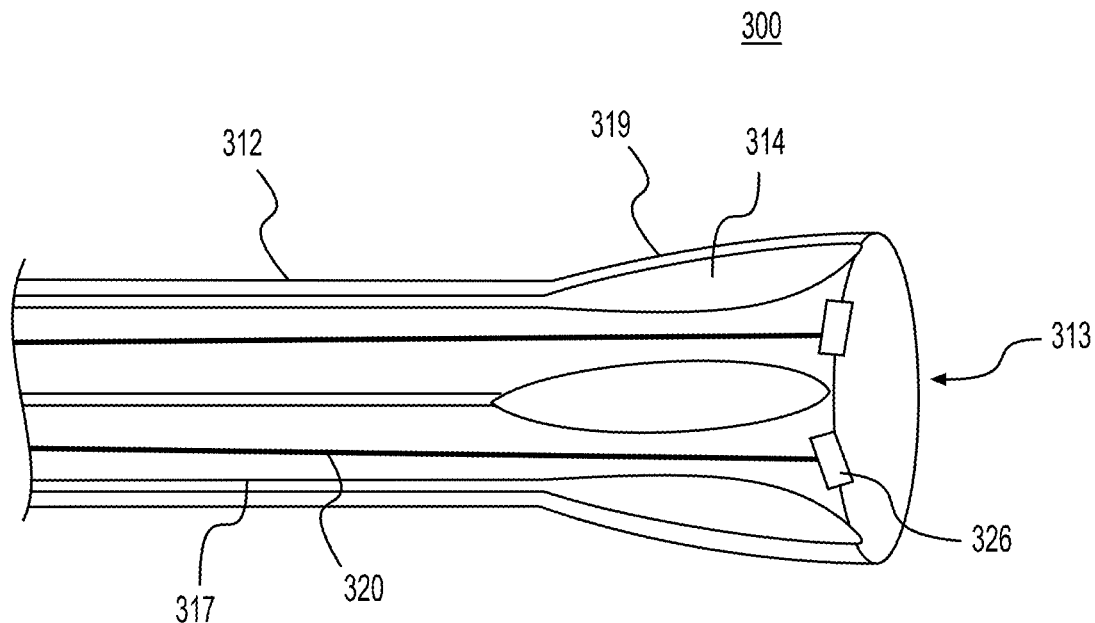
FIG. 3A is a is a perspective view of an embodiment of a transseptal insertion device with multiple balloons and hypotubes connected to the multiple balloons.
Figure 3B:
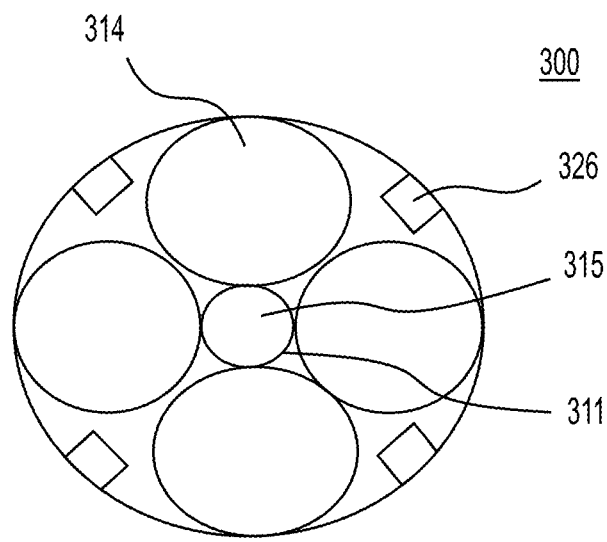
FIG. 3B is a is a front view of an embodiment of a transseptal insertion device with multiple balloons and hypotubes connected to the multiple balloons.

With reference to FIGS. 3A and 3B, shown is transseptal insertion device 300 including multiple balloons 314, which surround center lumen shaft 311 that defines center lumen 315, and sheath or catheter shaft 312 that includes center lumen shaft 311 and hypotubes 317 connected to multiple balloons 314. FIG. 3A is a side view of sheath or catheter shaft 312, and FIG. 3B is a front cross-sectional view of sheath or catheter shaft 312. Balloons 314 are in various shapes such as round, cylindrical, spherical, tear drop shaped or pear shaped, and are in various lengths. Balloons 314 may be with or without overhang over shaft. Balloons 314 are positioned around distal tip or end 313, and may extend around circumference of distal tip or end 313. Multiple balloons 314 are connected to one or more hypotubes 317, and inflated or deflated via hypotubes 317 that are contained in sheath or catheter shaft 312. Each of balloons 314 may be connected to corresponding hypotube 317 to independently control the inflation and deflation of balloons 314. Alternatively, balloons 314 may share one or more hypotubes 317. Inflation fluid or gas may flow through hypotubes 314 to inflate or deflate balloons 314. Outer covering 319 may cover the multiple balloons 314.

In between balloons 314, there are one or more ultrasound chips or transducers 326 that provide ultrasound imaging or visualizing capability. For illustrative purposes, FIG. 3B shows ultrasound chips or transducers 326 disposed between balloons 314, but ultrasound chips or transducers 326 may be deployed in or on balloons 314. Ultrasound chips or transducers 326 may be affixed to interior or exterior surface of balloon 314. Ultrasounds chips or transducers 326 may be ultrasound transceivers that both emit and receive waves, convert the ultrasound waves to electrical signals, transmit the electrical signals, e.g., through wire 320 that runs inside sheath or catheter shaft 312. However, ultrasound chips or transducers 326 may be connected wirelessly via WiFi or other wireless connection, to an external imaging device that produces images from the received signals (both still and video images).

Ultrasound chips or transducers 326 may be designed in the shape of the balloons 314. The balloons 314 may be round, cylindrical, spherical, tear drop shaped or pear shaped with overhang or without overhang. Ultrasound chips or transducers 326 may have shapes corresponding to the shapes of balloons 314. Alternatively, one or more ultrasound chips or transducers 326 may be deployed in a shape corresponding to the shapes of balloons 314. Depending on the shapes of balloons 314, ultrasound chips or transducers 326 may be side facing, front facing or back facing. Ultrasound chips or transducers 326 may be arranged in a line, disc, or cross-shape. Ultrasound chips or transducers 326 may be arranged to be forward facing (e.g., on distal end of balloon facing towards interatrial septum), or in a different direction/orientation, such as sideways and forward facing (e.g., facing towards interatrial septum and facing perpendicular to the distal or front end).

Orientations of ultrasound chips or transducers 326 may depend on whether balloons 314 are inflated or not. When balloons 314 are fully inflated, ultrasound chips or transducers 326 may be forward facing. However, when balloons 314 are deflated, ultrasound chips or transducer 326 may be folded flat and positioned on side of distal tip 313 of center lumen 315. Hence, when balloons 314 are deflated, ultrasound chips or transducer 326 may be side-facing. During inflation, orientation of ultrasound chips or transducers 326 may change as balloons 314 inflate (moving from side-facing orientation to forward facing orientation). Accordingly, operator(s) of transseptal insertion device 300 may vary the inflation of balloons 314 to achieve different orientations of ultrasound chips or transducers 326 for different imaging views.

Figure 4:
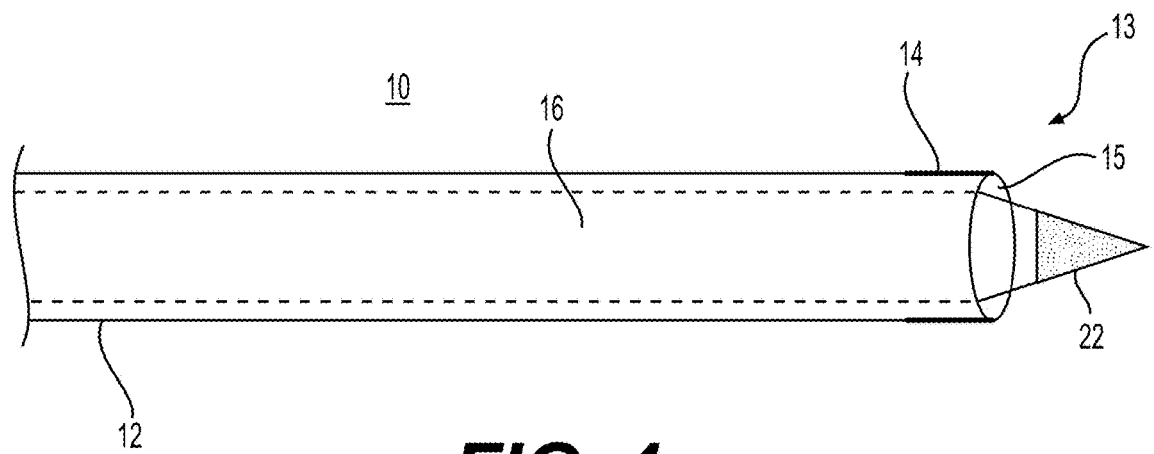
FIG. 4 is a perspective, cross-sectional view of an embodiment of a transseptal insertion device with radiofrequency energy capability.

With reference now to FIG. 4, shown is an embodiment of transseptal insertion device 10 with radiofrequency (RF) energy capability. Transseptal insertion device 10 shown includes sheath 12, overhanging one or more balloons 14, and dilator 16. Dilator 16 may include cap or crown 22, on distal end as shown, with RF energy capability or capable of delivering RF energy. Alternatively, cap or crown may include or be an RF electrode. Dilator 16 may be connected, e.g., on proximate end (not shown) to a radiofrequency energy source (not shown) at, e.g., external hub, that provides RF energy to cap or crown 22. The RF energy may be delivered through dilator 16. So equipped with cap or crown 22, dilator 16 may tent interaxial septum and create puncture of interaxial septum through delivery of RF energy. In this embodiment, the use of a sharp needle may be avoided. The dilator with cap or crown on distal end with RF energy capability or capable of delivering RF energy may be used for transseptal insertion devices 200 and 300 shown in FIGS. 2A-2B and 3A-3B.

Figure 5:
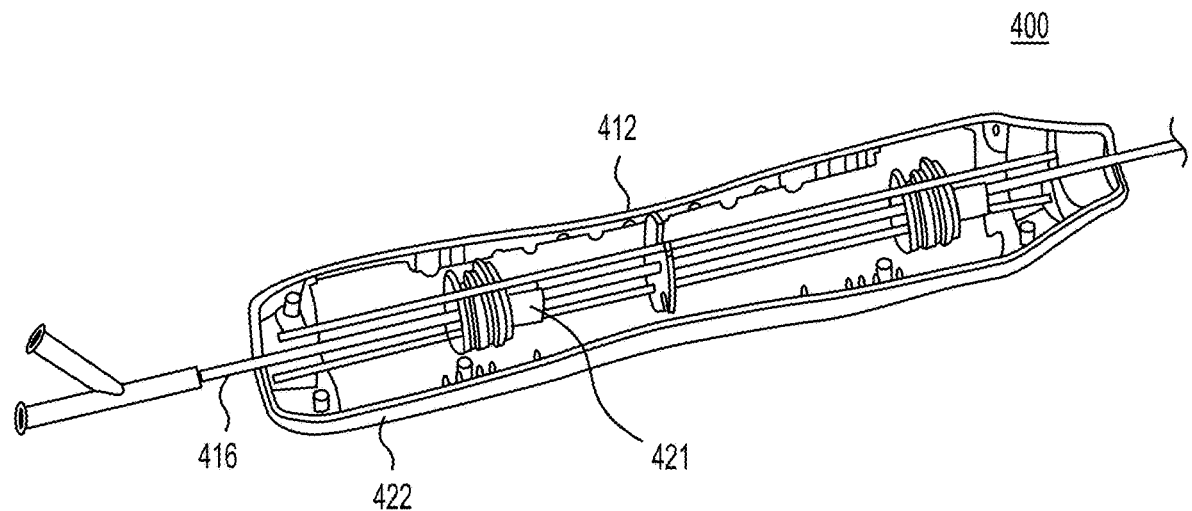
FIG. 5 is a is a perspective view of an embodiment of a transseptal insertion device with a drive assembly coupled to dilator, and knob coupled to the drive assembly.

With reference to FIG. 5, shown is transseptal insertion device 400 including drive assembly 421, which is coupled to dilator 416, and knob 422 coupled to drive assembly 421 to cause dilator 416 to traverse along an axial direction of sheath or catheter shaft 412. Dilator 416 may move backwards or forwards along the axial direction of sheath 412 while knob 422 is rotated. The drive assembly 421 may include nut assembly to drive the dilator 416. Dilator 416 may be with or without RF energy capability.

Figure 6:
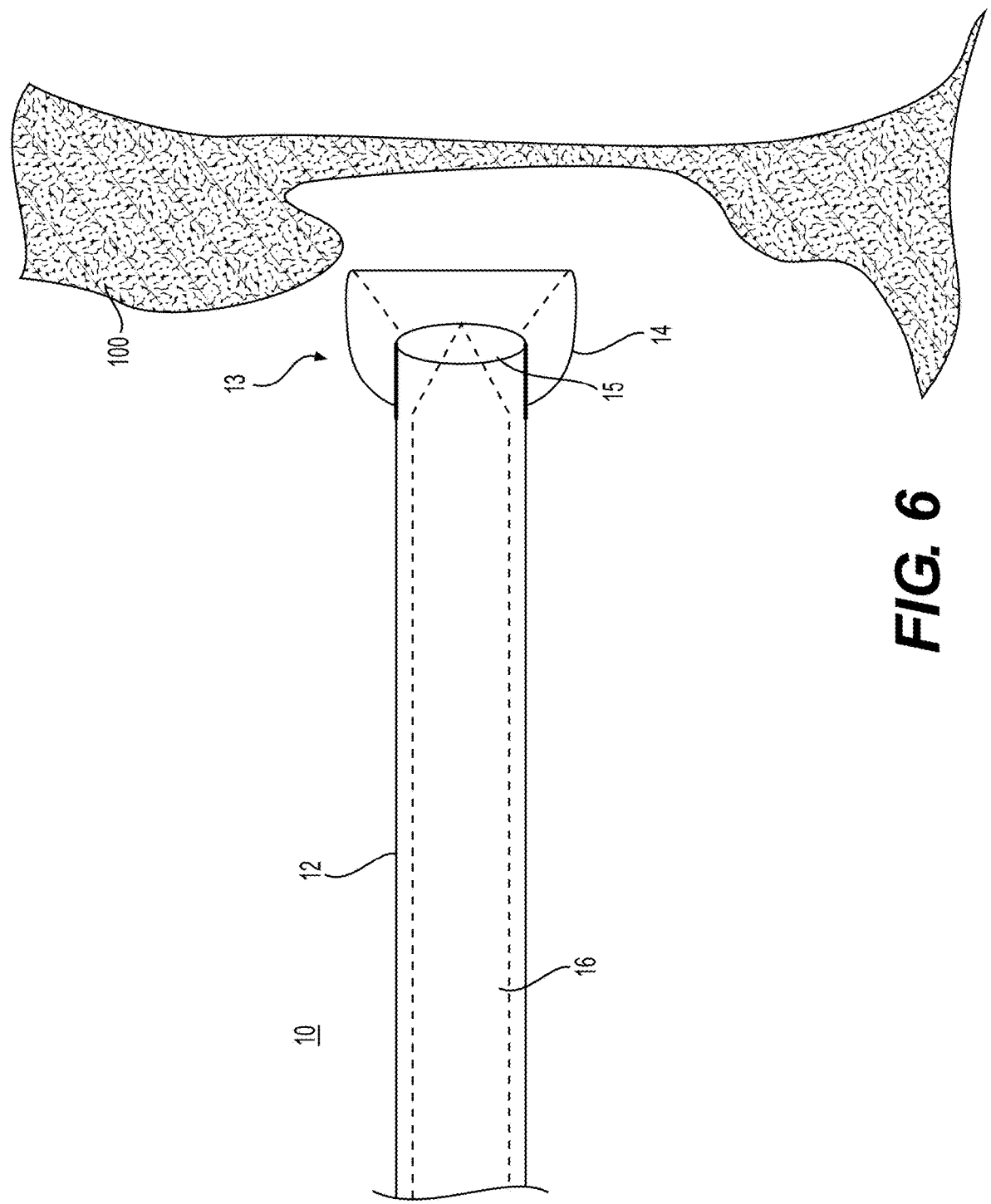
FIG. 6 is a perspective, cross-sectional view of an embodiment of a transseptal insertion device showing inflated overhanging balloon and dilator positioned within device and subplanar to overhanging balloon.

With reference now to FIG. 6, shown is distal end of an embodiment of transseptal insertion device 10 in which overhanging balloons 14 is inflated by supplying gas or fluid into balloon 14 through hypotube (not shown). Dilator 16 is shown positioned within center lumen 15 of sheath 12 with tip of dilator 16 positioned at distal tip 13 of transseptal insertion device 10 and sub-planar to overhanging balloon 14. The plane that is referred to here is the plane perpendicular to the axis of transseptal insertion device 10 and dilator 16, formed by the end of overhanging balloon 14. Hence, dilator 16 remains sub-planar to overhanging balloon 14 until operator intends balloon 14 to be deflated and dilator 16 to tent and puncture interatrial septum 100. As noted above, balloon 14 preferably extends completely around circumference of tip 13 of transseptal insertion device 10. Accordingly, FIG. 7 only illustrates cross-section of inflated balloon 14.

Figure 7:
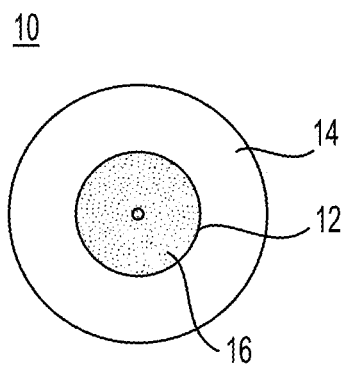
FIG. 7 is a cross-sectional, end view of an embodiment of a transseptal insertion device and dilator shown prior to puncturing an interatrial cardiac septum with inflated overhanging balloon.

With reference now to FIG. 7, shown is a front, cross-sectional view of distal end an embodiment of transseptal insertion device 10 in which overhanging balloon 14 is inflated. As shown, inflated overhanging balloon 14 preferably extends around entire circumference of sheath 12 (and, therefore, device 10). Shown situated within lumen 15 of sheath 12 is tip of dilator 16. Tip of dilator 16 is positioned within tip 13 of transseptal insertion device 10, as it would be prior to being extended past tip 13 and puncturing an interatrial cardiac septum.

Figure 8:
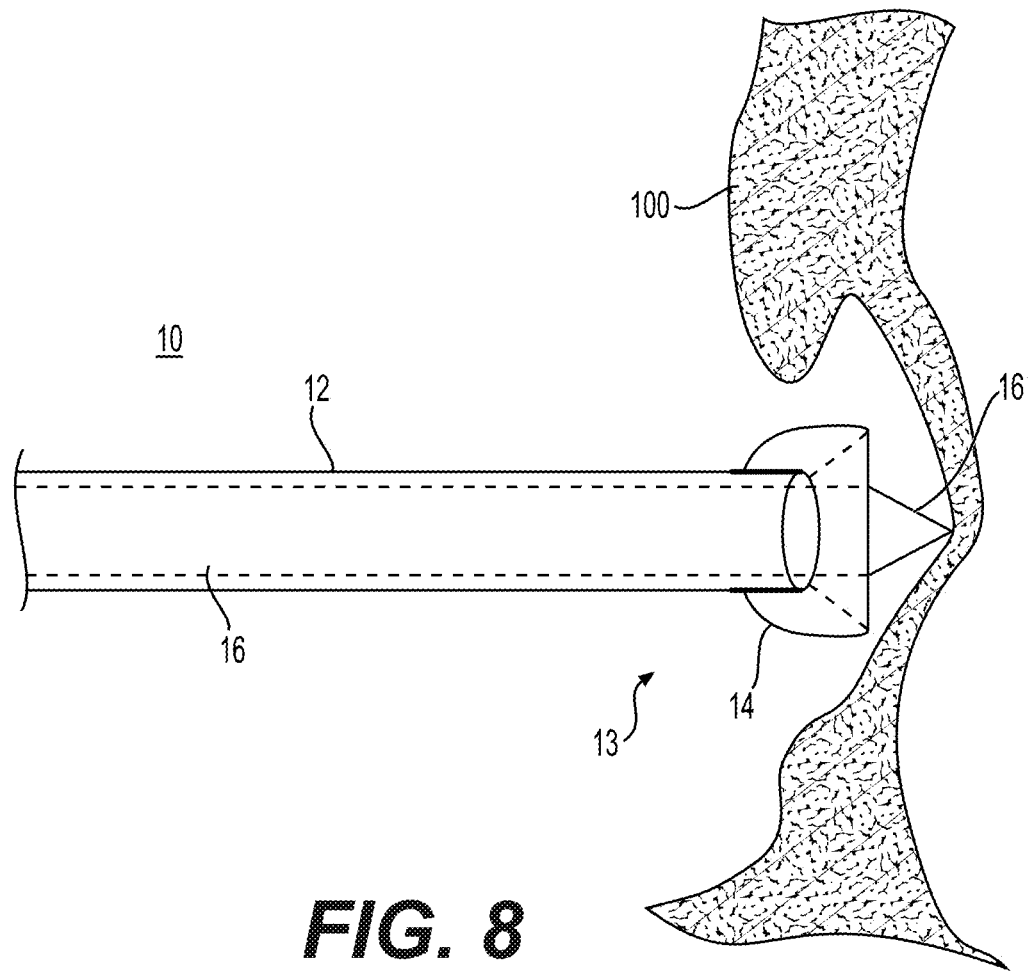
FIG. 8 is a perspective, cross-sectional view of an embodiment of a transseptal insertion device with dilator advanced forward in order to tent an interatrial septum.

With reference now to FIG. 8, shown is distal end of an embodiment of transseptal insertion device 10 with dilator 16 advanced forward in order to tent the interatrial septum 100. Dilator 16 is shown extending through center lumen 15 of sheath 12 and past overhanging balloon 14. At this stage, balloon 14 may be deflated by removing gas or fluid in balloon 14 through hypotube. Extended as such, and pressed against interatrial septum 100, dilator 16 tents the interatrial septum 100 away from transseptal insertion device 10.

Figure 9:
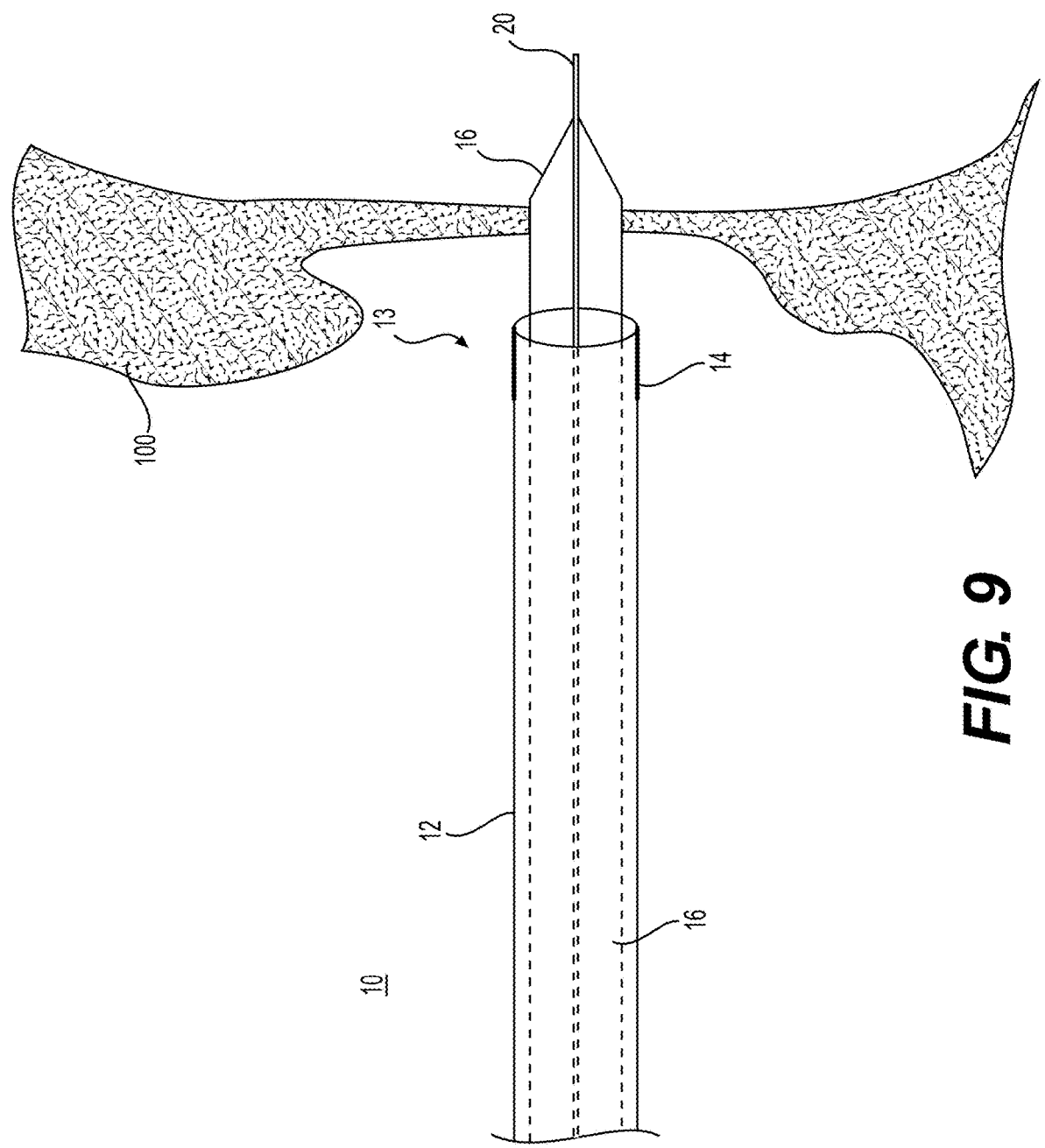
FIG. 9 is a perspective, cross-sectional view of an embodiment of a transseptal insertion device with a transseptal wire advanced post-puncture through interatrial septum.

With reference now to FIG. 9, shown is shown is distal end of an embodiment of transseptal insertion device 10 with dilator 16 advanced forward through interatrial septum 100, after puncturing septal wall (e.g., through application of energy through dilator 16 as described herein) and transseptal wire or wire rail 20 extending through dilator 16 and into left atrium chamber 110. Wire rail 20 may sit in a lumen 19 of dilator 16. Dilator 16 may be used as a conduit to advance the wire rail 20 into the left atrium.

Wire rail 20 may act as a guide for devices to enter the left atrium through the puncture in the septal wall made by transseptal insertion device 10. For example, wire rail 20 may guide transseptal insertion device 10 or other catheters in the left atrium. In this manner, catheters may be advanced safely into the left atrium over or guided by wire rail 20. In an embodiment, wire rail 20 may be energized (e.g., to ablate or puncture the septum with energy delivered from source at proximal end of transseptal insertion device 10).

With continued reference to FIG. 9, dilator 16 preferably defines and includes an opening or lumen 19 extending through its tip and through which transseptal wire 20 extends. With dilator 16 extended as shown and tenting interatrial septum, septum may be punctured by energy delivered through cap or electrode at tip of dilator 16 and transseptal wire rail 20 extended through opening in tip of dilator 16 and through puncture made in interatrial septum by dilator 16 cap.

With reference to FIGS. 10A-10C, shown are different views of an embodiment of transseptal insertion device 10 with a flexible sheath 12 flexed or angulated at different angles. Transseptal insertion device 10 may be flexed or angulated depending on the anatomy of the atria using fixed angled dilators 16 that are inserted into lumen shaft of sheath 12, causing sheath 12 to flex. Such fixed angled dilators 16 may be, e.g., any angle from 0-270°. Alternatively, sheath 12, lumen shaft and dilator 16 may be all flexible (preferably, hypotubes, needle and catheter inserted through such flexible sheath 12 are flexible or malleable, at least in part) and transseptal insertion device 10 may be flexed or angulated, thereby flexing or angulating sheath 12 and dilator 16, using, e.g., a handle or wire (not shown) connected to tip 13 of device 10. Handle and/or wire may also be used to turn or flex or move tip 13 of transseptal insertion device 10, e.g., moving tip 13 of sheath "up" or "down" or "left" or "right" or angulating tip 13 relative to axis of sheath 12 as shown.

Figure 11:
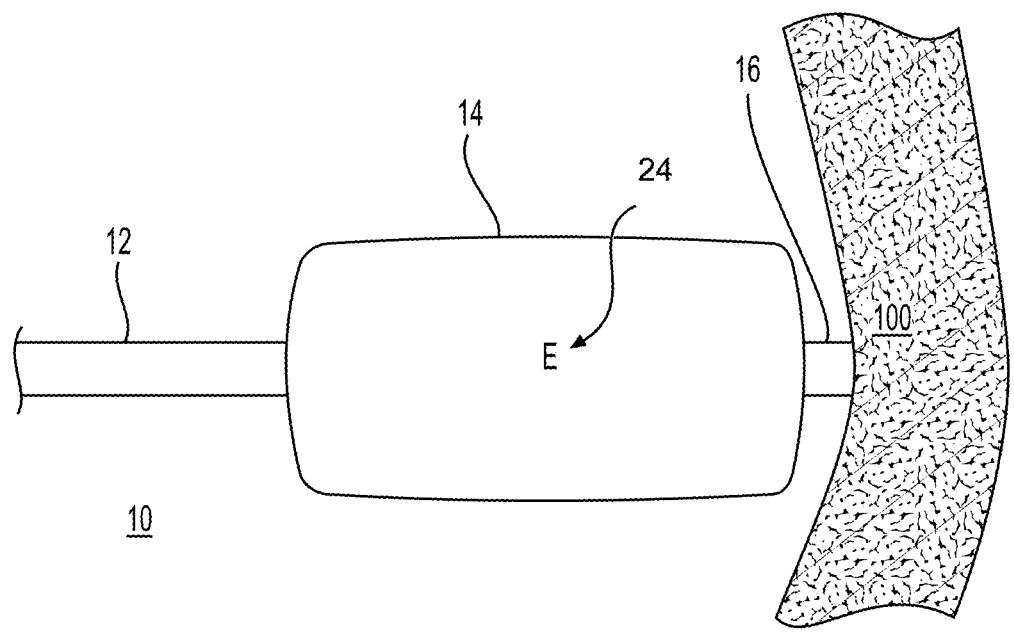
FIG. 11 is a side view of an embodiment of transseptal insertion device with an overhanging balloon with marking.

With reference now to FIG. 11, shown is distal end of an embodiment of transseptal insertion device 10 with inflated overhanging balloon 14. Balloon 14 shown is an embodiment with one or more markers 24. Marker 24 may be, e.g., a radiopaque and/or echogenic marker 24. As a radiopaque or echogenic marker, marker 24 will be visible on scanners used by those performing cardiac catheterizations. The markers 24 may be in the form of letters, such as an E or a C. Marker 24 enables the appropriate positioning of balloon 14 and sheath 12 in the 3-dimensional space (e.g., of the atrium) using imaging to view the marker 24 and, therefore, the position of balloon 14.

Specifically, in operation, the less posterior distal tip 13 is positioned, the more of the E (or C) will be shown. As operator of transseptal insertion device 10 turns or rotates distal tip 13 toward posterior of patient, less of the arms of the E will be seen. In a preferred embodiment, when only the vertical portion of the E is visible (i.e., appearing as an I) distal tip 13 will be rotated to its maximum posterior position.

With continuing reference to FIG. 11, balloon 14 is shown as inflated. However, distal end of dilator 16 is shown extruding or extending distally from balloon 14, past plane formed by distal end of inflated balloon 14. According, dilator 16 has been moved into the tenting and puncturing position, adjacent to interaxial septum. At this stage, balloon 14 may be deflated or will soon be deflated, and puncture of the interaxial septum is imminent.

Figure 12:
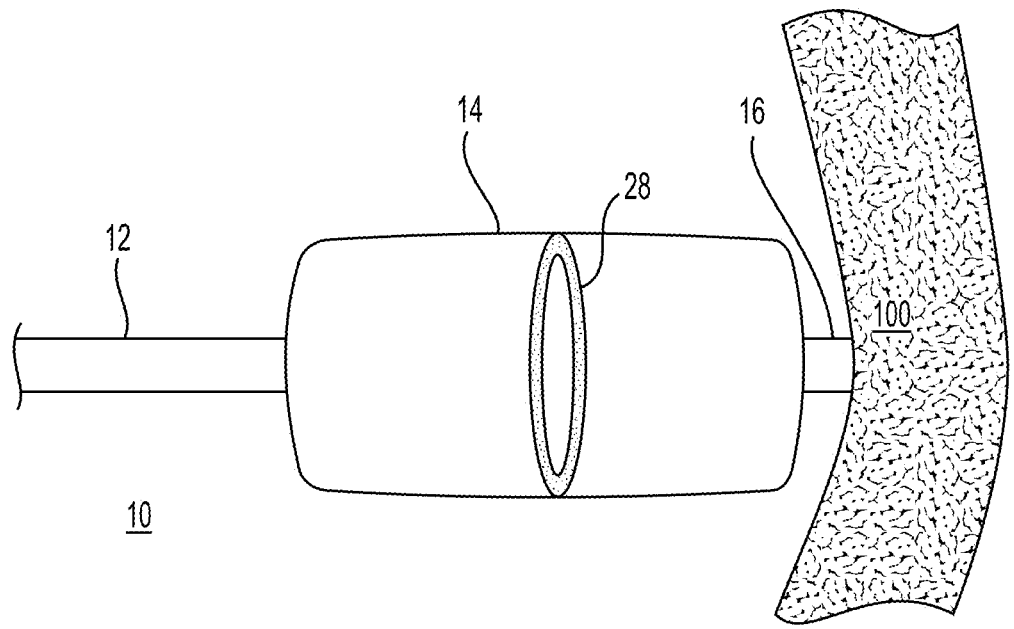
FIG. 12 is a side view of an embodiment of transseptal insertion device with an overhanging balloon with a marker band.

With reference now to FIG. 12, shown is another embodiment of overhanging balloon 14 which may be deployed in embodiments of transseptal insertion device 10. Overhanging balloon 14 may include ring or band 28 around a portion of balloon 14. Ring or band 28 may serve as a marker, similar to markers 24 shown in FIG. 11. Hence, ring 28 may be radiopaque or echogenic and may be view by scanning devices used for visualization in cardiac catheterizations (e.g., fluoroscopic imaging devices). Similar to the letter E or C, the view of the ring 28 changes as the distal tip 13 of transseptal insertion device 10 moves more posterior. When in a least posterior position, ring 28 may appear as just a line or band positioned across axis of transseptal insertion device 10. When device 10 is rotated so that distal tip 13 is significantly closer to the posterior, ring 28 may appear as a full "flat" circle or ring. In FIG. 12, distal tip 13 is partially rotated so that ring 28 is partially visible.

With reference to both FIGS. 11 and 12, the marker 24 and ring 28 are described and shown as located on balloon 14. In embodiments, marker 24 and/or ring 28 may also be located on sheath 12 and/or dilator 16. So located, marker 24 and/or ring 28 would operate in effectively the same manner as described above (i.e., the arms of the E would disappear as the distal end was moved more to the posterior and the ring would become more visible). Markers 24 and/or rings 28 may be placed on all of balloon 14, sheath 12, and dilator 16, or a combination thereof.

Figure 13:
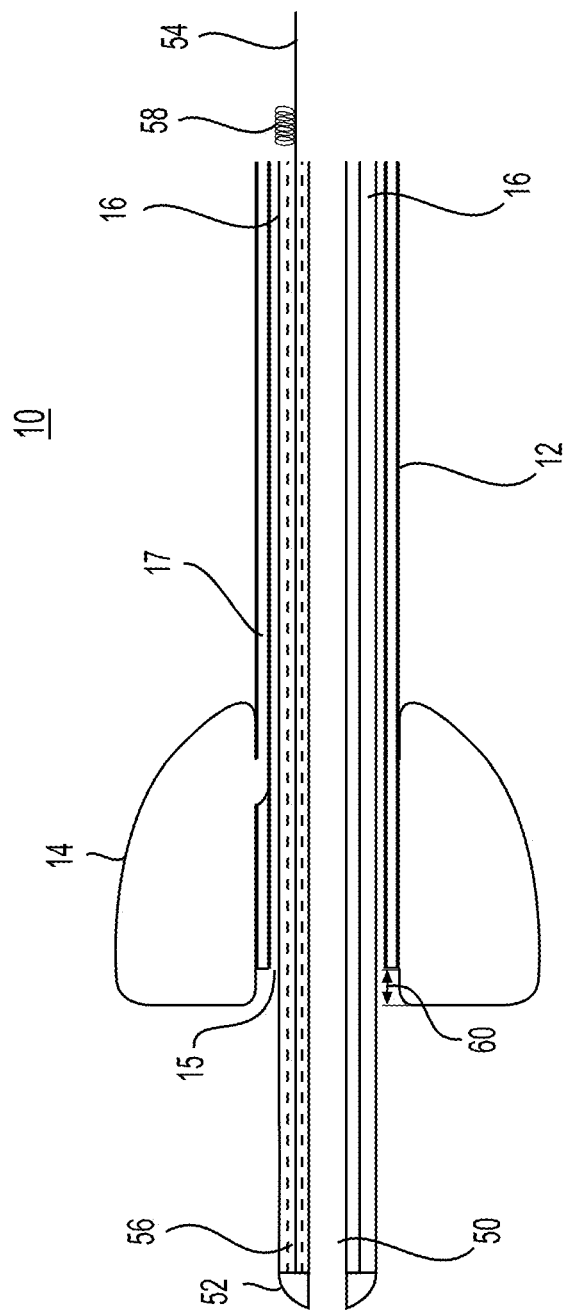
FIG. 13 is a cross-sectional side view of an embodiment of a transseptal insertion device that includes a dilator with an electrode tip.

With reference now to FIG. 13, shown is distal end of an embodiment of transseptal insertion device 10 that includes dilator 16 with electrode tip. Shaft of dilator 16 defines and contains a center lumen 50. Lumen 50 may be defined in the range of, but not limited to, 0.020 to 0.040 inches. Dilator 16 may be made from a polymer material (e.g., HDPE, LDPE, PTFE, or combination thereof). Dilator shaft 16 shown includes a distal electrode tip 52. Electrode tip 52 may be comprise a metallic alloy (e.g., PtIr, Au, or combination thereof). In preferred embodiments, the size and shape of electrode tip 52 is selected to be sufficient to generate a plasma for in vivo ablation of tissue in an applied power range of, but not limited to, 20-30 W. Electrical conductor 54 extends from electrode tip 52 to the proximal end (not shown) of the dilator 16. Electrical conductor 54 may run axially through an additional lumen 56 defined by and contained in dilator shaft 16. Electrical conductor 54 may contain a coil feature 58 to accommodate lengthening during bending or flexing of dilator 16.

Attached to distal end of sheath 12 is contains overhanging balloon 14 that is connected to hypotube 17. Overhanging balloon 14 may be made from a polymer material (e.g., PET, Nylon, Polyurethane, Polyamide, or combination thereof). Overhanging balloon 14 may be in the range of, but not limited to, 5-20 mm in diameter and 20-30 mm in length. Overhanging balloon 14 may be inflated via injection of gas or fluid through hypotube 17 connected to balloon 14. Overhanging balloon 14 may be deflated by removing gas or fluid in balloon 14 through hypotube 17 connected to balloon 14. During the proper functioning or operation of transseptal insertion device 10 for puncturing the interatrial septum, balloon 14 may be deflated when dilator 16 moves out of lumen 15 by removing gas or fluid from balloon 14. Overhanging balloon 14 is of form such balloon 14 overhangs or extends from distal end 13 of sheath 12. Overhang or extension 60 may be in the range of, but not limited to, 0.0 mm-5.0 mm. The end of the overhang or extension 60 is the plane to which dilator 16 remains sub-planar until moving to tent and puncture the interatrial septum.

Figure 14:
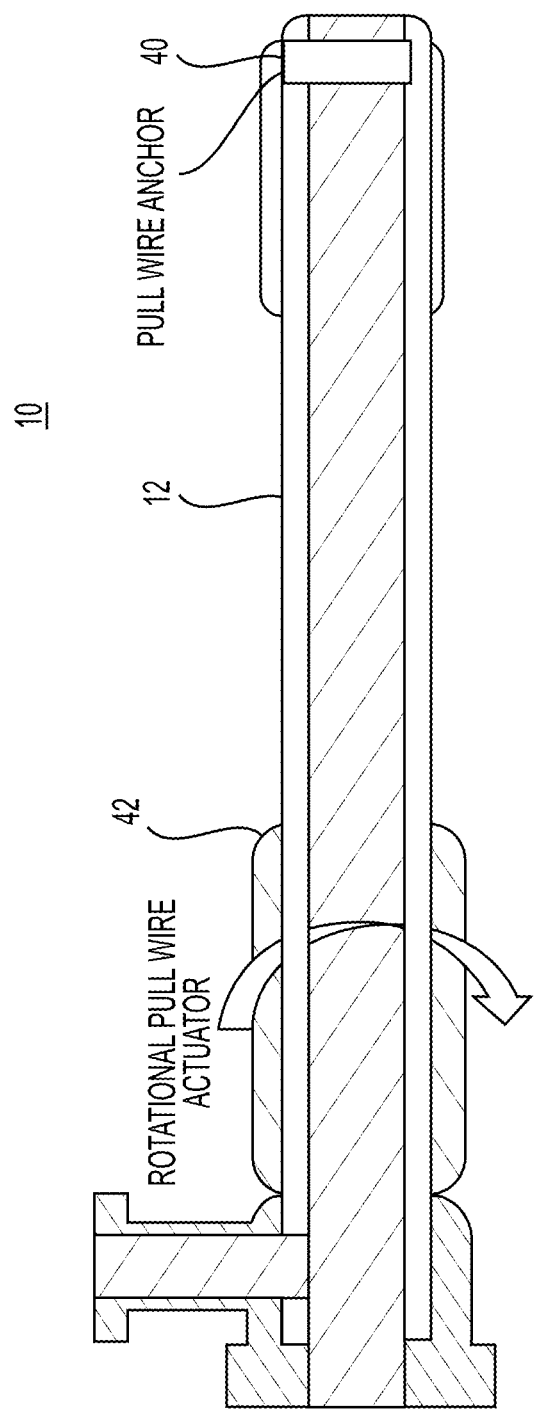
FIG. 14 is a side view of an embodiment of a transseptal insertion device with mechanical deflection capability.

With reference now to FIG. 14, shown is an embodiment of transseptal insertion device 10 that includes a mechanical deflection mechanism. Mechanical deflection mechanism may enable distal end of sheath 12 to be deflected or angulated to various angles with respect to axis of transseptal insertion device 10. Mechanical deflection mechanism may include a pull wire anchor 40 affixed to distal end of sheath 12 and pull wire actuator 42 connected to pull wire anchor 40 with pull wire (not shown). Rotation of pull wire actuator 42, as shown, may exert force on pull wire anchor 40 that deflects or angulates distal end of sheath 12. Pull wire actuator 42 may be rotated by handle connected thereto (not shown). Deflection or angulation of distal end of sheath 12 may enable better intersection (e.g., more perpendicular, flush) with interaxial septum and, therefore, better puncture and insertion by transseptal insertion device 10.

Figure 15:
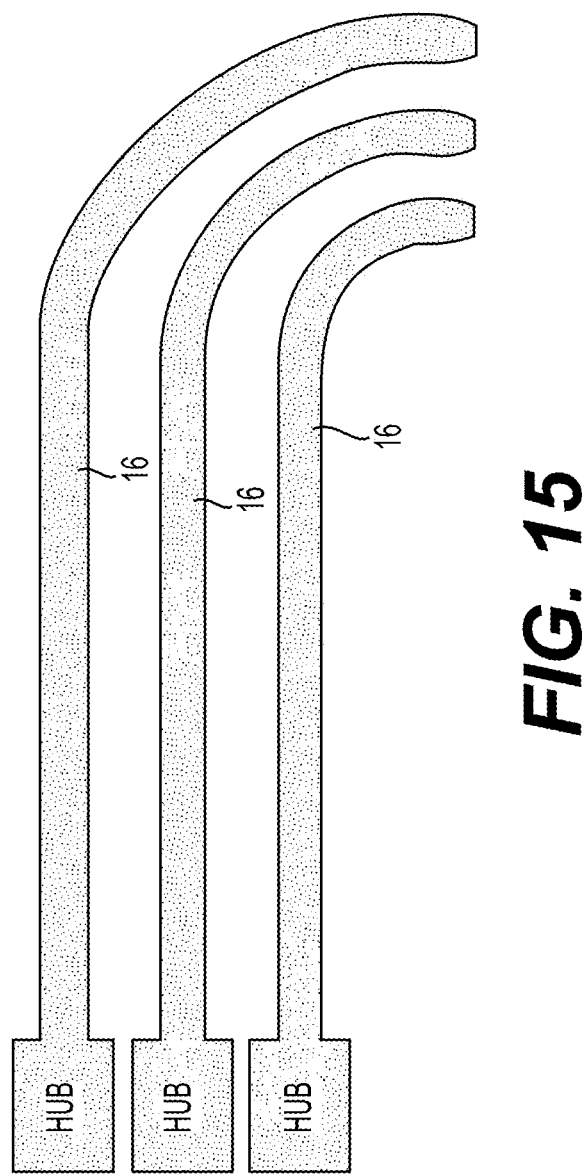
FIG. 15 is side views of embodiments of curved dilators that may be used in embodiments of a transseptal insertion device.

With reference now to FIG. 15, shown are three (3) embodiments of curved dilators 16, each with a different curve profile (i.e., different angle of deflection or curve). Curved dilators 16 may be used in embodiments of transseptal insertion device 10 with flexible or malleable sheath 12. Such a flexible or malleable sheath 12 may be referred to as a steerable sheath 12 as it is "steered" by curved dilator 16 inserted in sheath 12.

Figure 16:
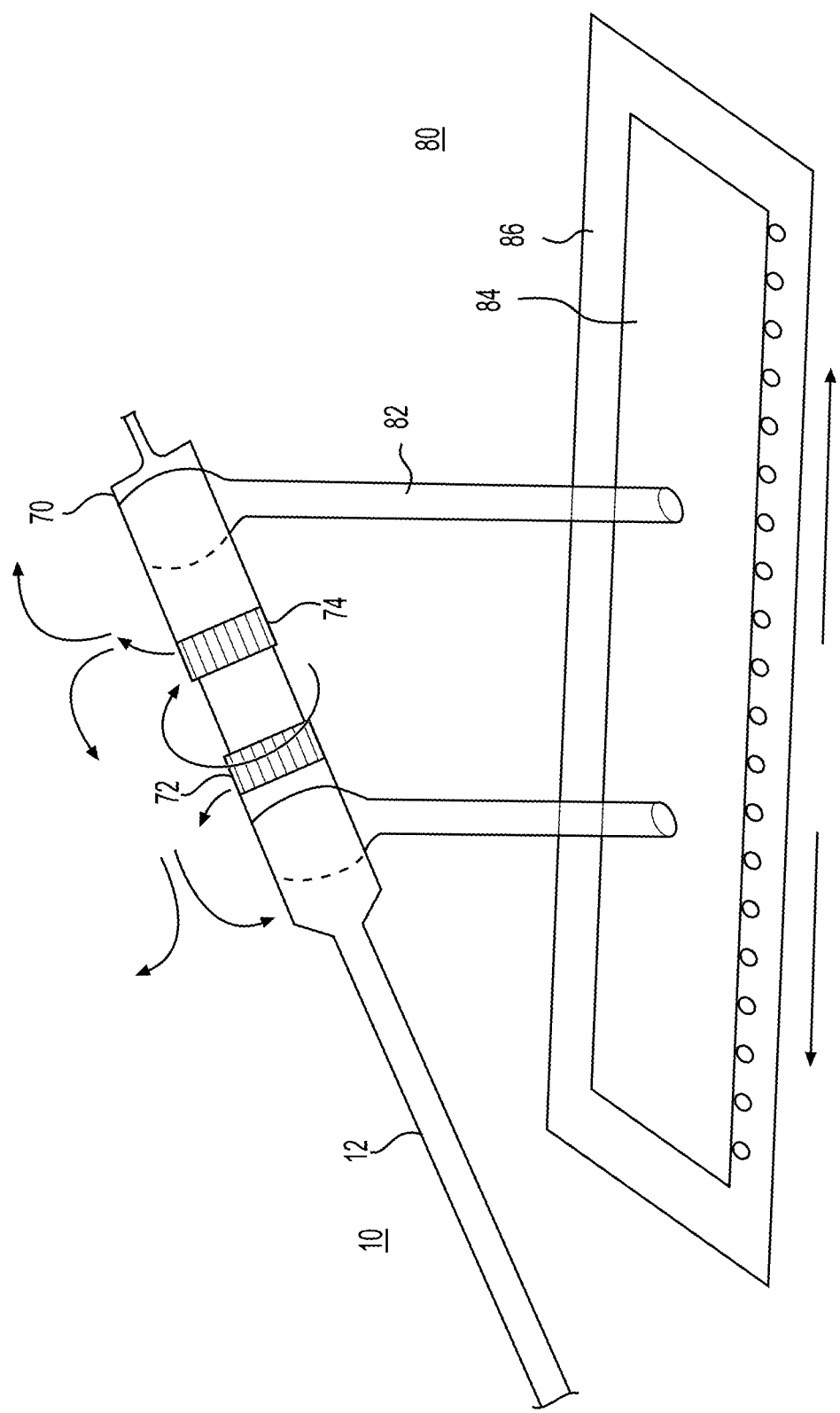
FIG. 16 is a perspective side view of a proximal end of an embodiment of a transseptal insertion device showing a handle and a stabilizer.

With reference now to FIG. 16, shown is an embodiment of transseptal insertion device 10 with an external stabilizer 80. Stabilizer 80 keeps proximal end of transseptal insertion device 10 stable while allowing movement of transseptal insertion device 10 towards the distal and proximal ends of device 10, rotational/torqueing movement of proximal end of device 10, and manipulation of dials or other controls of device 10. In effect, stabilizer 80 substantially prevents unwanted movement of the transseptal insertion device 10 and, importantly, distal end of sheath 12, balloon 14, and dilator 16.

Stabilizer 80 includes connecting rods or arms 82 that connect stabilizer 80 to handle 70 at proximal end of transseptal insertion device 10. Connecting arms 82 are attached to stabilizer platform 84. Connecting arms 82 preferably hold the handle 70 securely and tightly, while permitting desired rotational movements and control manipulation. Stabilizer platform 84 is moveably attached to stabilizer base 86 so that stabilizer platform 84, and hence handle 70 and transseptal insertion device 10, may be slid forwards and backwards along axis of transseptal insertion device 10 towards and away from insertion point in patient (typically femoral vein at the groin of patient). Stabilizer base 86 is typically secured to a flat, stable surface, such as a table, or the leg of the patient. Configured as such, stabilizer 80 prevents unwanted vertical, rotational, or other movement of transseptal insertion device 10 and its handle 70, keeping transseptal insertion device 10 and its handle 70 stable while permitting precise manipulation of handle 70 and its controls.

With continuing reference to FIG. 16, as shown, proximal end of transseptal insertion device 10 may include a handle 70 for control and manipulation of transseptal insertion device 10 and, particularly, dilator 16 and distal end of dilator 16. Handle 70 may include a dial 72 that may be used to turn or deflect distal end of dilator 16, effectively moving the distal end of dilator 16 up or down in relation to axis of transseptal insertion device 10 (as indicated by arrows in FIG. 16). Handle 70 may also include dial 74 for extruding/extending distal end of dilator 16 out of sheath 12 and retracting dilator 16 back into sheath 12, effectively moving dilator 16 along axis of transseptal insertion device 10 (as indicated by arrows in FIG. 16). Handle 70 may also be rotated, as indicated by rotational arrow in FIG. 16, in order to deflect or turn distal end of transseptal insertion device to left or right in relation to axis of transseptal insertion device 10, increasing or decreasing dilator 16 angle of deflection in that direction. If dial 72 moves distal end of dilator 16 along Y axis, and transseptal insertion device 10 axis is considered the Z axis, so that dial 74 moves dilator 16 along Z axis rotating handle 70 moves distal end of transseptal insertion device 10 (and hence distal end of dilator 16) along X axis. Handle 70 includes a port through which dilator 16 and other devices inserted into transseptal insertion device 10 may be inserted. Handle 70 may also include one or more tubes or other ports permitting connection to external hubs and external energy sources, inflation liquids or gas.

In embodiments shown herein, balloon 14 and dilator 16 may be used as energy sources in the left atrium and may be used to deliver energy to the pulmonary veins, left atrial appendage, mitral valve and the left ventricle present in the left atrium. Such embodiments may include external energy sources connected to balloon 14 and/or dilator 16 through wires or other conductors extending lumen in sheath 12. Delivery of energy via balloon 14 or dilator 16 may be thermal/Cryo or radiofrequency, laser or electrical. The delivery of such energy could be through a metallic platform such as a Nitinol cage inside or outside balloon 14. Transseptal insertion device 10 may also include an energy source external to the proximal end of the sheath and operatively connected to balloon 14 to deliver energy to balloon 14.

Figure 17B:
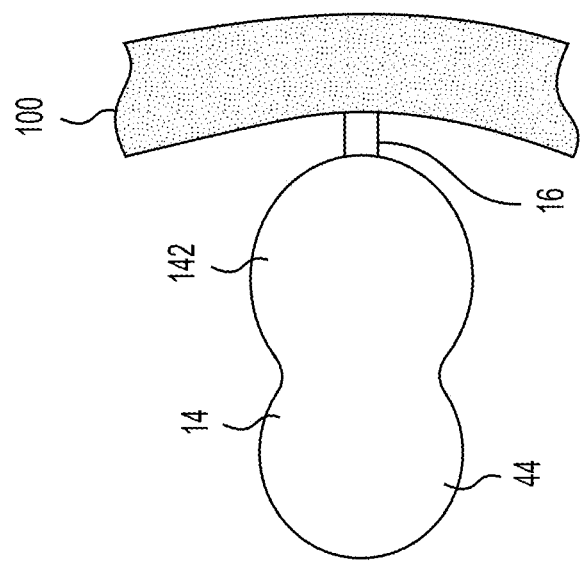
FIGS. 17A-17B are side views of an embodiment of a transseptal insertion device with balloons capable of differential inflation.
Figure 17A:
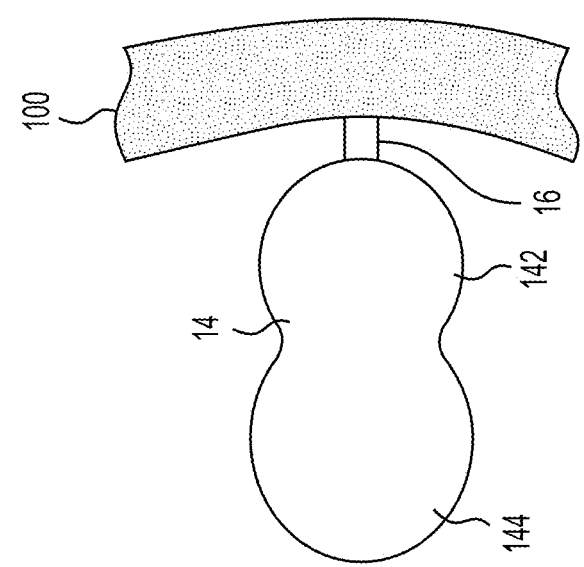

With reference now to FIGS. 17A and 17B shown is an embodiment of transseptal insertion device 10 enabling differential expansion of balloon 14. Differential expansion of balloon 14 enables balloon 14 inflation to be adjusted based on the needs of the device operator and the conditions present in the patient's heart. For example, the size of the fossa ovalis portion of the interatrial septum may dictate the desired size of the inflated balloon 14 needed at the puncture site (interatrial septum if often punctured through the fossa ovalis). Fossae can vary greatly in size. The larger the fossa, the harder it will be to tent the interatrial septum with balloon 14. Large fossa tend to be saggy and more difficult to manipulate. Hence, with a large fossa, a larger distal end of balloon 14 will make proper tenting of the interatrial septum easier. Indeed, it may be ideal to have balloon 14 inflated uniformly until intersecting or passing through fossa and then differentially expanding distal end 142 of balloon 14 to move fossa out of the way. In FIG. 17A, distal end or portion 142 of balloon 14 is smaller (less expanded) than proximal end 144 of balloon 14.

Oppositely, the smaller the fossa, the easier it will be to tent the interatrial septum but, there will be less room to maneuver balloon 14 near interatrial septum. Consequently, a smaller distal end of balloon 14 is desired. It also may be beneficial to expand the proximal portion 144 more in order to help fix or secure balloon 14 in place. In FIG. 17B, distal end or portion of balloon 14 is larger (more expanded) than proximal end or portion of balloon 14. In both FIGS. 17A and 17B, dilator 16 has extruded from sheath 12 and past distal end of balloon 14, tenting interatrial septum 100, and puncture is imminent.

This differential expansion of balloon 14 may be achieved, e.g., by using different materials for different portions of balloon 14 (e.g., a more expandable material for distal end 142 than proximal end or portion 144, or vice versa). In general, balloon 14 may be made of either compliant or non-compliant material, or a combination thereof. Compliant material will continue expanding as more inflating liquid or gas is added to balloon 14 (at least until failure). Non-compliant material will only inflate up to a set expansion or designated inflation level. Combinations of compliant and non-compliant material may be used to provide a differentially expanding balloon 14. For example, distal end 142 may be formed from compliant material and proximal end 144 from non-compliant material to enable a larger distal end 142. Oppositely, proximal end 144 may be formed from compliant material and distal end 142 from non-compliant material to enable a larger proximal end 144. Other means for providing differential expansion of balloon 14 may be used, such as applying energy to different portions of balloon 14 to increase or decrease the compliance, and expandability, of that portion.

Balloon 14 may also be used to direct other equipment into these anatomical locations or be used as an angiographic or hemodynamic monitoring balloon. Differential expansion of balloon 14 may be utilized for proper orientation or direction of such equipment.

Figure 18:
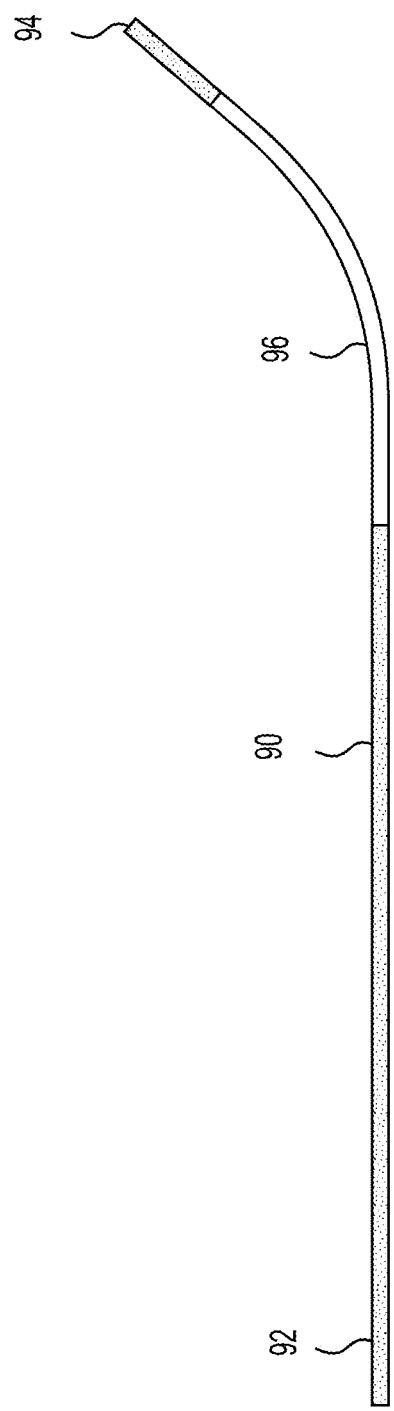
FIG. 18 is a side view of a malleable or flexible transseptal needle that may be used in embodiments of a flexible transseptal insertion device with multiple angulations.

With reference now to FIG. 18, shown is an embodiment of a malleable transseptal needle 90 that may be used with transseptal insertion device 10 with a flexible sheath or otherwise capable of multiple angulations. In embodiments, malleable transseptal needle 90 may be of a variety of diameters and lengths. For example, embodiments include an 18 gauge transseptal needle and that is available in 71 cm, 89 cm, and 98 cm lengths. In embodiments, the malleable transseptal needle 90 has different stiffness in a proximal segment 92, distal segment 94, and in a middle segment 96 between. For example, malleable transseptal needle 90 may be stiffer in the proximal segment 92 and distal segment 94 and more flexible (less stiff) in a middle segment or midsection 96. The mid-section may be the section where transseptal insertion device 10 and dilator 16 angulate. In an embodiment, malleable transseptal needle 90 is used and a control handle provided that enables three-dimensional movements. Malleable transseptal needle 90 shown is, preferably, malleable or flexible at least in part. Proximal end 92 of malleable transseptal needle 90 may be stiff (e.g., made from a stiff material, such as a metal). Mid-section or middle 96 of malleable transseptal needle 90 may be malleable or flexible (e.g., made from a flexible, malleable material, such as rubber). Accordingly, mid-section may flex or bend, enabling malleable transseptal needle 90 to pass through angulated or flexed sheath 12.

Distal end 94 of malleable transseptal needle 90 (i.e., end that punctures interatrial cardiac septum) may be stiff with a cap or electrode at its tip for delivering energy to interatrial septum to puncture interatrial septum. In embodiments, transseptal needle is able to transmit radiofrequency energy to create a controlled septal puncture. Such a transseptal needle may or may not be malleable, but is able deliver RF energy through a cap or crown (e.g., an electrode) at its distal end tip. Embodiments of malleable transseptal needle 90 may include a stiff and sharpened end for mechanically or physically piercing or puncturing the interatrial septum. The needle 90 may be connected, e.g., on proximate end (not shown) to a radiofrequency (RF) energy source (not shown) at, e.g., external hub, that provides RF energy through needle to its distal end tip. In such an embodiment, dilator 16 may tent interaxial septum and RF energy capable transseptal needle may create puncture of interaxial septum through delivery of RF energy.

Embodiments may include an additional dilator which would be able to dilate the distal end of sheath 12, or the entire sheath length, thereby significantly increasing the French size of the sheath 12. For example, balloons deployed within sheath 12 may be inflated to expand sheath 12. In such embodiments, transseptal insertion device 10 may, therefore, be used to accommodate and deliver larger devices or be able to retrieve devices once they have been extruded from sheath 12 and have embolized. Such balloons may be inflated through one or more hypotubes.

In embodiments, energy, typically electrical energy, may directed through transseptal insertion device 10 may be used to increase or decrease the French size of sheath 12. In such embodiments, sheath 12 is fabricated from materials that are known to increase in malleability and or expand when certain energies are applied. In this manner, the French size of sheath 12 may be adjusted to a size deemed necessary during a given procedure. Such energy may be applied through wires or conductive material, connected to energy source external to proximal end of transseptal insertion device 10, attached to or fabricated within sheath 12 or other components of transseptal insertion device 10. Likewise, parts or portions of transseptal insertion device 10 may be selectively made more rigid or more malleable/soft with the application of energy. Therefore, with the application of differential energy to different parts of transseptal insertion device 10 at different times, transseptal insertion device 10 size may be adjusted to enable various devices that are ordinarily larger and bulkier than the catheter to traverse through the catheter. In embodiments, transseptal insertion device 10 may accommodate devices up to 36 Fr.

In an embodiment of transseptal insertion device 10, visualization of an intrathoracic region of interest using MRI techniques may be provided. Embodiments may, for example, provide a needle system comprising a hollow needle having a distal portion and a proximal portion, said distal portion having a distal-most end sharpened for penetrating a myocardial wall. The needle may include a first conductor, an insulator/dielectric applied to cover the first conductor over the proximal portion of said needle and a second conductor applied to cover the insulator/dielectric. The method may further direct the needle system into proximity to a myocardial wall, track progress of the needle system using active MRI tracking, penetrate the myocardial wall to approach the intrathoracic region of interest, and, use the needle system as an MRI antenna to receive magnetic resonance signals from the intrathoracic region of interest.

In related embodiments, MRI antenna may be installed on distal tip 13 of sheath 12, dilator 16 or on balloon 14, similar to ultrasound chips or transducers 226 or 326 described above. Wires connecting such MRI antenna or other MRI components may pass through lumen in dilator 16 or sheath 12 and connect with appropriate magnetic resonance energy source on exterior of distal end of transseptal insertion device 10.

Figure 20A:
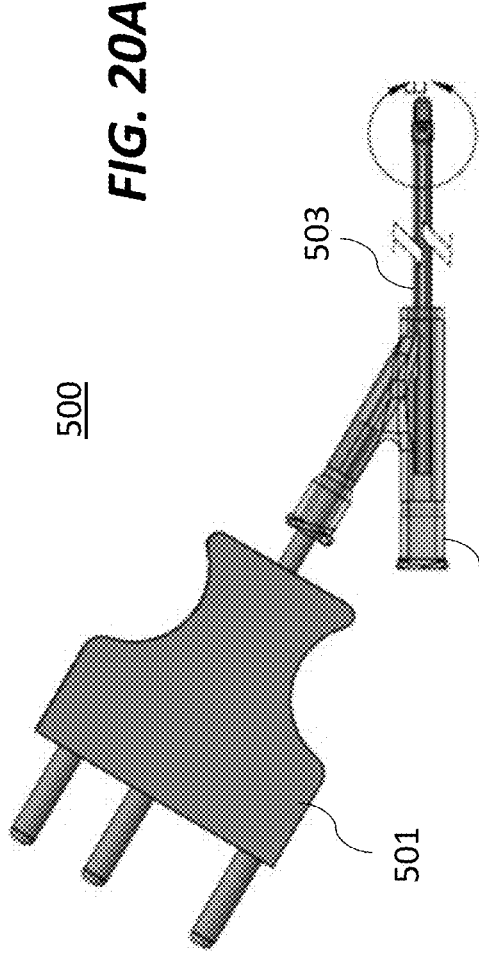
FIGS. 20A-20C are a side view, a cross-sectional end view, and a close side view of a puncture tip of an embodiment of an improved transseptal puncture system with puncture member balloon seal with an inflated puncture member balloon.
Figure 20B:
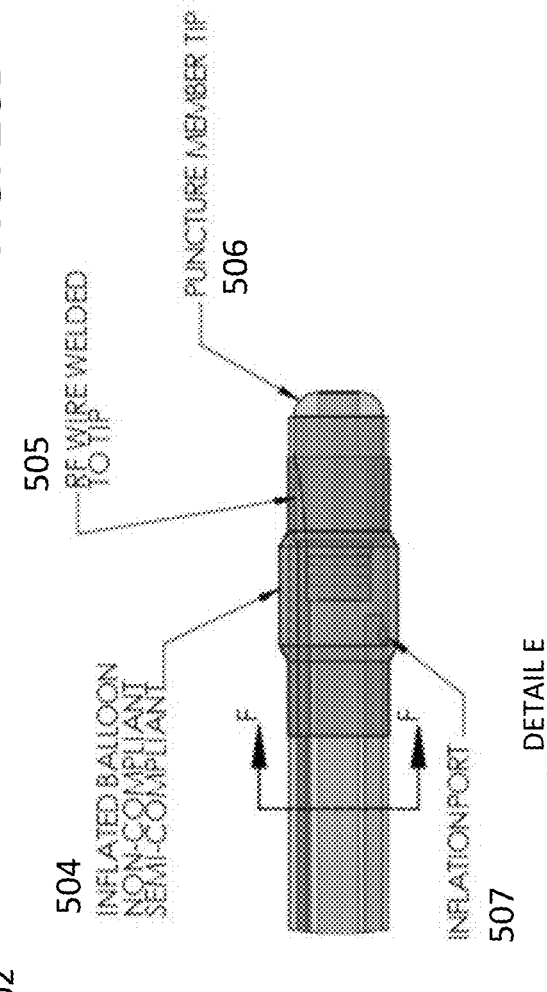
Figure 20C:
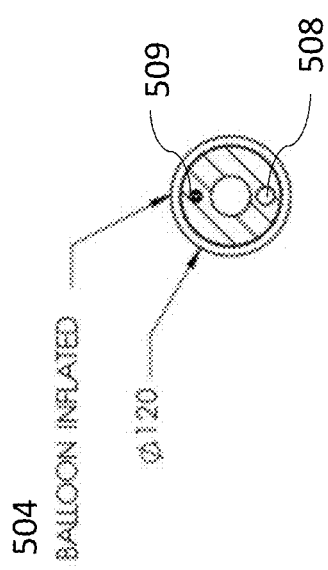

With reference to FIGS. 19A-20C, shown are an embodiment of an improved transseptal puncture device 500 with puncture member balloon seal 504. With reference to FIGS. 19A-19C, shown are a side view, a close-in side view of the section C, and a cross-sectional view of the section D-D of the transseptal puncture device 500, respectively, when the puncture member balloon 504 is deflated. With reference now to FIGS. 20A-20C, shown are a side view, a close-in side view of the section E, and a cross-sectional view of the section F-F of the transseptal puncture device 500, respectively, when the puncture member balloon 504 is inflated.

Figures 21A, 21B:
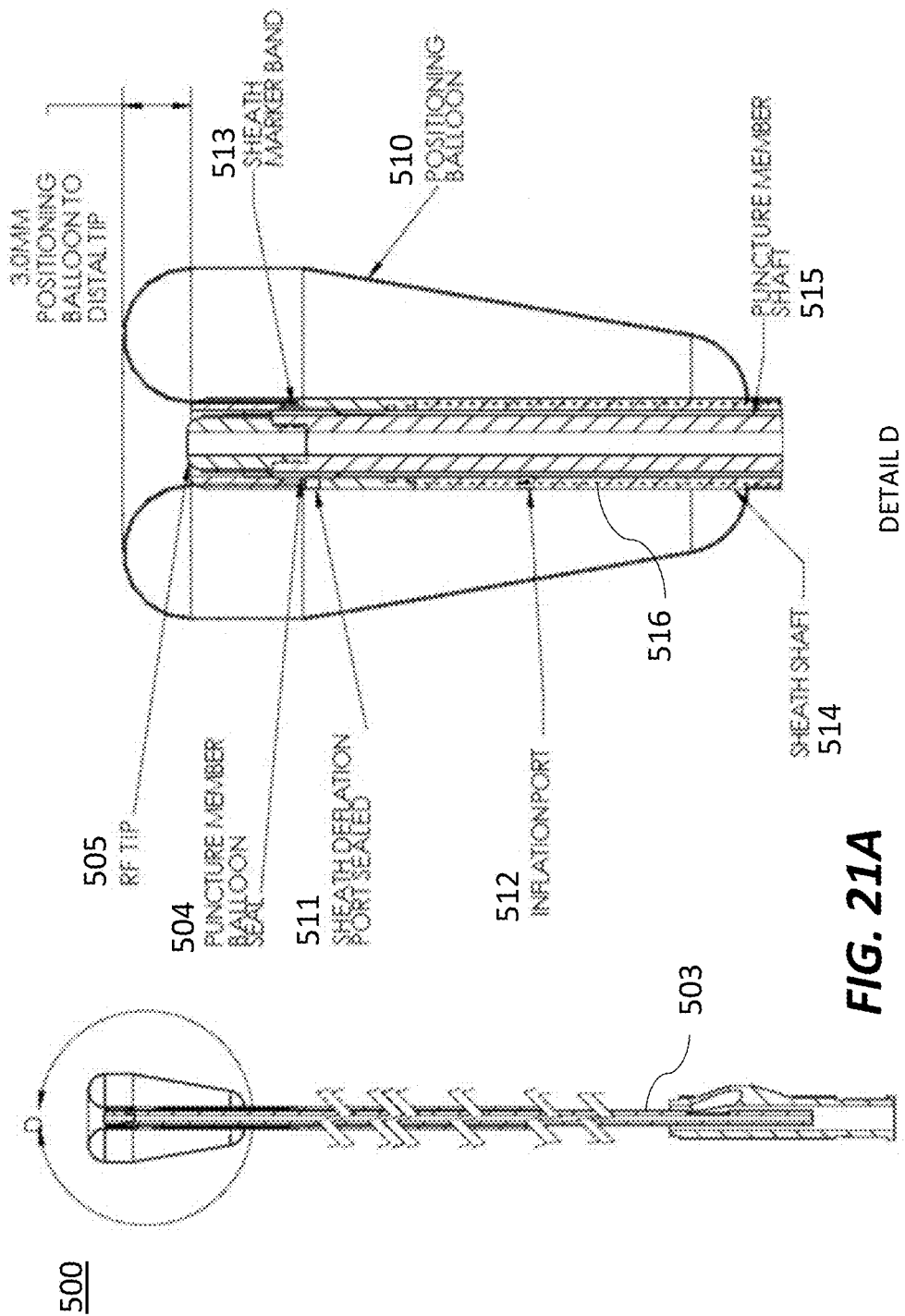
FIGS. 21A-21B are cross-sectional side view and a close, cross-sectional side view of a puncture tip of an embodiment of an improved transseptal puncture system with puncture member balloon seal with an inflated positioning balloon.

Referring to FIGS. 19A-20C, the transseptal puncture device 500 includes a radiofrequency (RF) generator plug 501, Y-connector 502, and puncture member multi-lumen extension 503 that includes sheath 514 and puncture member 515 (see FIG. 21B). The RF generator plug 501 is connected to the puncture member multi-lumen extension 503 through a Y-connector 502, and provides power for a RF generator (not shown) that may be positioned in the puncture member 515 located in the multi-lumen extension 503. The puncture member 515 is located inside the sheath 514, and has a distal end 506 that is positioned toward the cardiac interatrial septum of the patient when the device 500 is in use. The puncture member balloon 504 is mounted on the puncture member 515 and is located near the distal end 506 of the puncture member 515. The close-in side view FIG. 19B and the cross-sectional view FIG. 19C show deflated puncture member balloon 504, while the close-in side view FIG. 20B and the cross-sectional view FIG. 20C show inflated puncture member balloon 504.

The puncture member 515 includes an inflation port 507 for inflating the puncture member balloon 504, and a lumen 508 which is connected to the inflation port 507 that supplies gas or fluid to the inflation port 507 to inflate the puncture member balloon 504. The puncture member 515 also includes at least one RF tip 505 at the distal end 506 of the puncture member 515. The RF tip 505 is capable of delivering RF energy. The RF generator (not shown) produces RF energy, and the RF energy is supplied to the RF tip 505. The puncture member 515 includes a lumen 509 for wires that delivers RF energy to the RF tip 505.

With reference to FIGS. 21A-21B, shown are a side view and a close-in side view of the section D of the transseptal puncture device 500, respectively, when the positioning balloon 510 is inflated. The puncture member multi-lumen extension 503 includes the sheath 514 and the puncture member 515. The sheath 514 may have the sheath marker band 513, and the puncture member balloon 504, which is mounted on the puncture member 515, may be aligned with the sheath marker band 513. The sheath 514 includes one or more positioning balloons 510, one or more inflation ports 512 connected to the positioning balloons 510, and at least one tube 516 that delivers gas or fluid to the inflation port 512 to inflate the positioning balloons 510. The tube 516 may be the hypotube 17 (see FIG. 13). The sheath 514 also includes one or more deflation ports 511 that is connected to the positioning balloons 510. When the puncture member balloon 504 is inflated, the inflated puncture member balloon 504 seals the one or more deflation ports 511 in the sheath 514, preventing leak from the positioning balloons 510 and permitting inflation of the positioning balloons 510. The position balloons 510 are then inflated through the inflation port 512 of the sheath 514. The non-compliant or semi-compliant puncture member balloon 504 seals off the deflation ports 511 of the sheath 514, allowing the positioning balloons 510 to inflate and position the distal end 506 of the puncture member 515 to the fossa ovalis (see FIG. 6 for example).

With reference to FIGS. 22A-22B, shown are a side view and a close-in side view of the section B of transseptal puncture device 500, respectively, when the puncture member 515 advances toward fossa ovalis. Once precisely positioned, the puncture member 515 is then pushed distally towards the fossa ovalis. The inflated puncture member balloon 504 moves away from the deflation ports 511, exposing the deflation ports 511. The positioning balloons 510 deflate through the deflation ports 511. However, the positioning balloons 510 may be deflated through both inflation ports 512 and the deflation ports 511.

With reference to FIGS. 23A-23D, shown are side views of distal end portion of the puncture member multi-lumen extension 503 of the transseptal puncture device 500 of the disclosed invention. The transseptal insertion device 500 includes a sheath 514 that defines at least one lumen 517 therein, one or more positioning balloons 510 that are connected to the distal end 506 of the sheath 514, a puncture member 515 movably positioned within the at least one lumen 517, and a puncture member balloon 504 mounted on the puncture member 515. The sheath 514 has one or more deflation ports 511 and one or more inflation ports 512. The inflation ports 512 are connected to at least one tube 516 that supplies gas or fluid to the positioning balloons 510. The puncture member 515 has an inflation port 507 through which gas or fluid is supplied to inflate the puncture member balloon 504. The puncture member balloon 504 may be deflated through the inflation port 507. The puncture member 515 defines a center lumen 518 therein, and a transseptal wire 519 is positioned inside the center lumen 518. The transseptal wire 519 has a distal end and is designed to and is capable of precisely puncturing the cardiac interatrial septum.

Figure 23A:
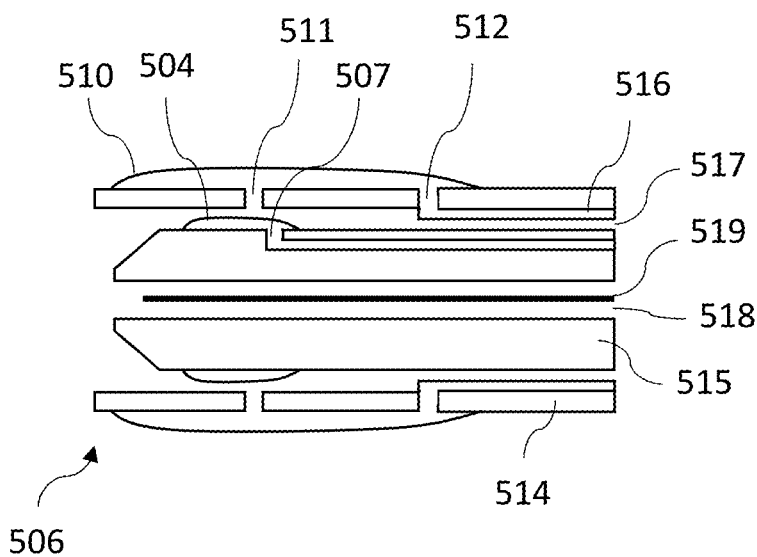
FIGS. 23A-23D are side views of distal end portion of the puncture member multi-lumen extension of the transseptal puncture device.
Figure 23B:
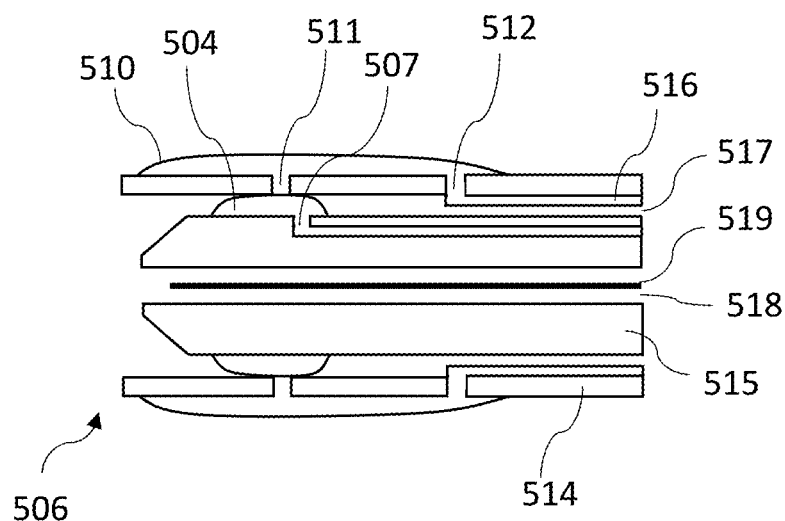
Figure 23C:
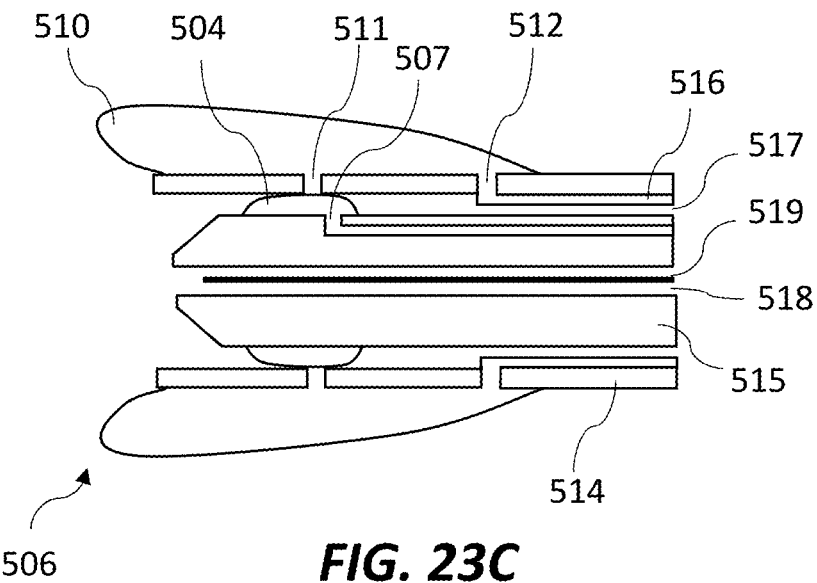
Figure 23D:
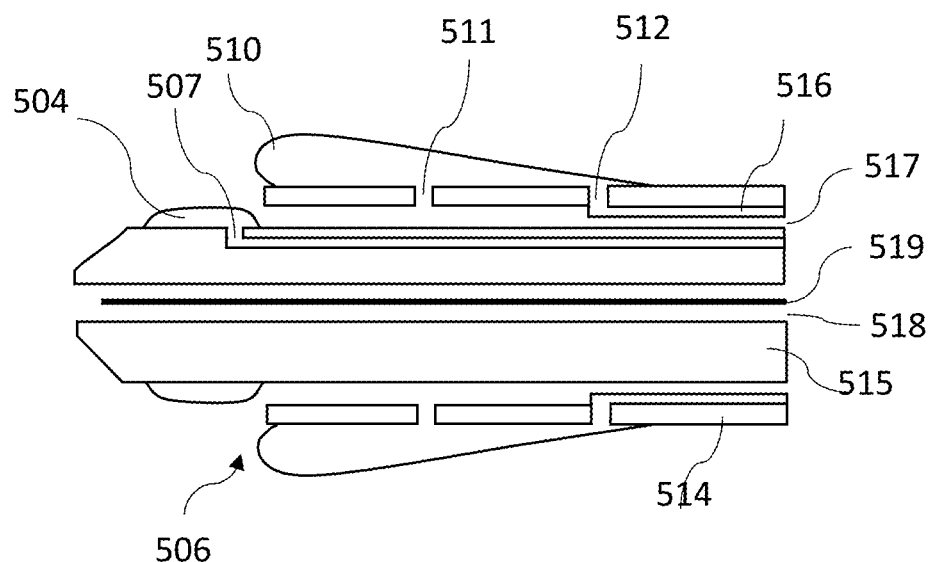

Referring FIG. 23A, the puncture member balloon 504 is deflated, and the deflation ports 511 are open. Referring to FIG. 23B, the puncture member balloon 504 is inflated sealing the deflation ports 511. Referring to FIG. 23C, the positioning balloons 510 are inflated by supplying gas or fluid through the inflation ports 512. Because the deflation ports 511 are sealed by the inflated puncture member balloon 504, the positioning balloons 510 can be inflated without leak. Referring to FIG. 23D, when the puncture member 515 advances forward, the inflated puncture member balloon 504 moves away from the deflation ports 511. Consequently, the deflation ports 511 is open, and the positioning balloons 510 begin to deflate through the deflation ports 511.

Figure 24:
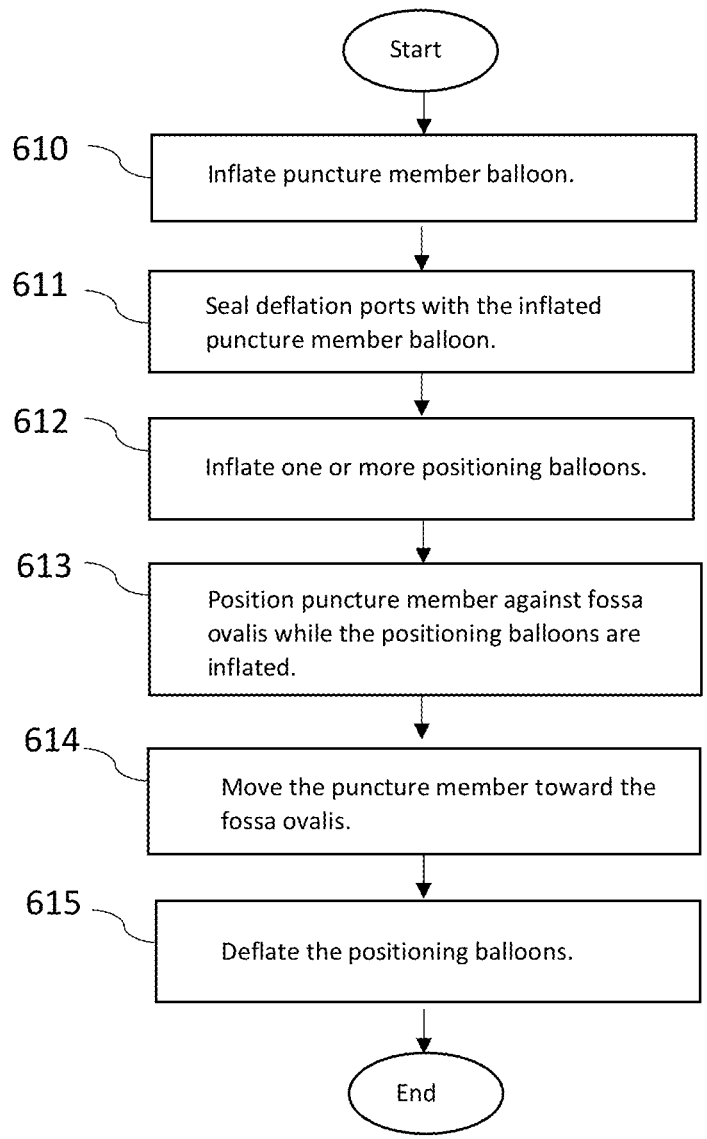
FIG. 24 is a workflow diagram for a method for suitably facilitating precise and safe transseptal puncture of a cardiac interatrial septum with a transseptal insertion device.

With reference to FIG. 24, shown is a workflow diagram for a method 600 for suitably facilitating precise and safe transseptal puncture of a cardiac interatrial septum with a transseptal insertion device. A puncture member balloon 504 located on a puncture member 515 is inflated, block 610. The puncture member 515 has a distal end that is positioned toward the cardiac interatrial septum of the patient. One or more deflation ports 511, which are located in a sheath 514, are sealed with the inflated puncture member balloon 504, block 611. One or more positioning balloons 510 connected to the distal end of the sheath 514 are inflated, block 612. The inflated positioning balloons 510 overhang and extend past the distal end of the sheath. The puncture member 515 is positioned against fossa ovalis of the cardiac interatrial septum while the positioning balloons are inflated, block 613. The puncture member 515 is moved toward the fossa ovalis, block 614. At this step, the distal end of the puncture member 515 extends past the overhanging one or more positioning balloons 510, and the puncture member balloon 504 moves away from the one or more deflation ports 511 while the puncture member 515 is advancing. The one or more positioning balloons 510 are deflated, block 615, while the distal end of the puncture member presses the fossa ovalis.

Since many modifications, variations, and changes in detail can be made to the described preferred embodiments of the invention, it is intended that all matters in the foregoing description and shown in the accompanying drawings be interpreted as illustrative and not in a limiting sense. Consequently, the scope of the invention should be determined by the appended claims and their legal equivalents.

What is claimed is:

1. A transseptal insertion device which is suitable for facilitating precise and safe transseptal puncture of a cardiac interatrial septum, comprising: a sheath having a distal end that is positioned toward the cardiac interatrial septum of a patient when the transseptal insertion device is in use and a proximal end that is external to the patient, and said sheath includes a lumen extending between said distal end and said proximal end of said sheath;
at least one positioning balloon extending radially outwardly from said sheath adjacent said distal end of the sheath, wherein said at least one positioning balloon is moveable from an inflated position to a deflated position wherein in said first inflated position the at least one positioning balloon overhangs and extends past the distal end of the sheath, preventing accidental puncturing of the cardiac interatrial septum and stabilizing the transseptal insertion device against fossa ovalis of the cardiac interatrial septum, and wherein
the sheath includes at least one deflation port positioned adjacent to said at least one positioning balloon to provide fluid communication between said at least one positioning balloon and said at least one lumen of said sheath wherein said at least one deflation port is configured to deflate the at least one positioning balloon when said at least one positioning balloon moves from said inflated position to said deflated position;
a puncture member extending longitudinally within the at least one lumen of said sheath wherein said puncture member has a distal end wherein said puncture member is movable from a retracted position wherein said distal end of said puncture member is within said at least one lumen of said sheath to an operative position wherein said distal end of said puncture member extends distally from said distal end of said sheath; and
a puncture member balloon extending radially outwardly from said puncture member adjacent said distal end of said puncture member and wherein said puncture member includes a port and a lumen, wherein said lumen is in fluid communication with said port to provide fluid communication between said puncture member lumen and said puncture member balloon, wherein the puncture member balloon is moveable from a deflated position to an inflated position wherein in said inflated position and when said puncture member is in said retracted position, the puncture member balloon is positioned adjacent said deflation port of the sheath and is configured to seal said deflation port of the sheath and said at least one positioning balloon is moveable from said deflated position to said inflated position and wherein when said puncture member is in said operative position, said puncture member balloon is positioned distally from said at least one deflation port of said sheath opening said at least one deflation port of said sheath and said positioning balloon is moveable from said inflated position to said deflated position.

2. The transseptal insertion device of claim 1 wherein the sheath includes one or more inflation ports to inflate the at least one positioning balloon.

3. The transseptal insertion device of claim 2 wherein said sheath comprises at least one hypotube connected to the at least one inflation port of the sheath, wherein the at least one positioning balloon is configured to be inflated by fluid supplied through the at least one hypotube.

4. The transseptal insertion device of claim 2 wherein the at least one deflation port of the sheath is positioned distal to the at least one inflation port of the sheath.

5. The transseptal insertion device of claim 1 wherein said puncture member includes a lumen extending from said distal end to a proximal end and comprises a transseptal wire positioned within said lumen of said puncture member, wherein the transseptal wire has a distal end configured to precisely puncture the cardiac interatrial septum.

6. The transseptal insertion device of claim 1 wherein the puncture member includes a radio frequency (RF) tip at the distal end of the puncture member, wherein the RF tip is configured to deliver RF energy.

7. The transseptal insertion device of claim 6 wherein the puncture member includes a RF generator that is configured to produce RF energy that is transmitted to the RF tip.

8. The transseptal insertion device of claim 1 further comprising at least one ultrasound transceiver on a surface of said positioning balloon that is configured to emit and to receive ultrasound waves, and to convert the ultrasound waves to electrical signals.

9. A method for suitably facilitating precise and safe transseptal puncture of a cardiac interatrial septum with a transseptal insertion device, comprising:
inflating a puncture member balloon located on a puncture member that has a distal end that is positioned toward the cardiac interatrial septum of the patient;
sealing one or more deflation ports located in a sheath with the inflated puncture member balloon;
inflating one or more positioning balloons connected to a distal end of the sheath, wherein the inflated one or more positioning balloons overhang and extend past the distal end of the sheath;

positioning the puncture member against fossa ovalis of the cardiac interatrial septum while the positioning balloons are inflated;

advancing the puncture member toward the fossa ovalis, wherein the distal end of the puncture member extends past the overhanging one or more positioning balloons, wherein the puncture member balloon moves away from the one or more deflation ports while the puncture member advances; and deflating the one or more positioning balloons while the distal end of the puncture member presses the fossa ovalis.

10. The method of claim 9 further comprising advancing a transseptal wire past the distal end of the puncture member to puncture the fossa ovalis, wherein the transseptal wire is positioned in a center lumen formed in the puncture member.

11. The method of claim 9 wherein the puncture member balloon is inflated by gas or fluid supplied through an inflation port located in the puncture member.

12. The method of claim 9 wherein the one or more positioning balloons are inflated by gas or fluid supplied through one or more inflation ports located in the sheath.

13. The method of claim 12 wherein the one or more deflation ports of the sheath are positioned closer to the distal end of the sheath than the one or more inflation ports of the sheath.

14. The method of claim 9 wherein the one or more positioning balloons are deflated through the one or more deflation ports of the sheath.

15. The method of claim 9 wherein the one or more positioning balloons are deflated through both the one or more deflation ports of the sheath and the one or more inflation ports of the sheath.

* * * * *